(12) United States Patent
Rariy et al.

(10) Patent No.: US 10,004,729 B2
(45) Date of Patent: *Jun. 26, 2018

(54) TAMPER-RESISTANT PHARMACEUTICAL COMPOSITIONS OF OPIOIDS AND OTHER DRUGS

(71) Applicant: COLLEGIUM PHARMACEUTICAL, INC., Canton, MA (US)

(72) Inventors: Roman V. Rariy, Philadelphia, PA (US); Alison Fleming, Mansfield, MA (US); Jane C. Hirsh, Wellesley, MA (US); Said Saim, New Milford, CT (US); Ravi K. Varanasi, Cumberland, RI (US)

(73) Assignee: COLLEGIUM PHARMACEUTICAL, INC., Canton, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/606,112

(22) Filed: May 26, 2017

(65) Prior Publication Data

US 2017/0319575 A1    Nov. 9, 2017

Related U.S. Application Data

(63) Continuation of application No. 14/320,086, filed on Jun. 30, 2014, now Pat. No. 9,682,075, which is a (Continued)

(51) Int. Cl.
*A61K 9/14* (2006.01)
*A61K 9/16* (2006.01)
(Continued)

(52) U.S. Cl.
CPC ............. *A61K 31/485* (2013.01); *A61K 9/14* (2013.01); *A61K 9/1617* (2013.01);
(Continued)

(58) Field of Classification Search
CPC .......... A61K 9/141; A61K 9/148; A61K 9/20; A61K 9/145; A61K 9/16; A61K 9/1617;
(Continued)

(56) References Cited

U.S. PATENT DOCUMENTS

| 2,404,319 A | 7/1946 | Shelton |
| 3,015,128 A | 1/1962 | Somerville, Jr. |

(Continued)

FOREIGN PATENT DOCUMENTS

| CA | 2273808 A1 | 9/2000 |
| EP | 0179583 A1 | 4/1986 |

(Continued)

OTHER PUBLICATIONS

"Castor oil, hydrogenated," European Pharmacopoeia V.5, p. 1197-1198 (2005).

(Continued)

*Primary Examiner* — Lakshmi Sarada Channavajjala
(74) *Attorney, Agent, or Firm* — Cooley LLP

(57) ABSTRACT

Tamper-resistant pharmaceutical compositions have been developed to reduce the likelihood of improper administration of drugs, especially drugs such as opioids. The tamper-resistant compositions retard the release of drug, even if the physical integrity of the formulation is compromised (for example, by chopping with a blade or crushing) and the resulting material is placed in water, snorted, or swallowed. However, when administered as directed, the drug is slowly released from the composition as the composition is passes through the GI tract.

19 Claims, 3 Drawing Sheets

Related U.S. Application Data continuation of application No. 12/965,572, filed on Dec. 10, 2010, now Pat. No. 8,840,928.

(60) Provisional application No. 61/285,231, filed on Dec. 10, 2009.

(51) Int. Cl.

| | |
|---|---|
| *A61K 31/44* | (2006.01) |
| *A61K 31/485* | (2006.01) |
| *A61K 9/48* | (2006.01) |
| *B29C 70/60* | (2006.01) |
| *A61K 9/50* | (2006.01) |
| *A61K 47/12* | (2006.01) |
| *A61K 47/44* | (2017.01) |
| *A61K 9/20* | (2006.01) |

(52) U.S. Cl.
CPC .......... *A61K 9/1635* (2013.01); *A61K 9/1641* (2013.01); *A61K 9/1664* (2013.01); *A61K 9/1694* (2013.01); *A61K 9/4808* (2013.01); *A61K 9/5042* (2013.01); *A61K 47/12* (2013.01); *A61K 47/44* (2013.01); *B29C 70/60* (2013.01)

(58) Field of Classification Search
CPC ...... A61K 9/50; A61K 9/2013; A61K 9/2077; A61K 31/135; A61K 31/485
See application file for complete search history.

(56) References Cited

U.S. PATENT DOCUMENTS

| | | | |
|---|---|---|---|
| 3,146,167 A | 8/1964 | Lantz, Jr. et al. | |
| 3,172,816 A | 3/1965 | Swintosky et al. | |
| 3,336,200 A | 8/1967 | Krause et al. | |
| 3,773,955 A | 11/1973 | Pachter et al. | |
| 3,966,940 A | 6/1976 | Pachter et al. | |
| 3,980,766 A | 9/1976 | Shaw et al. | |
| 4,070,494 A | 1/1978 | Hoffmeister et al. | |
| 4,457,933 A | 7/1984 | Gordon et al. | |
| 4,569,937 A | 2/1986 | Baker et al. | |
| 4,599,326 A | 7/1986 | Marvola et al. | |
| 4,675,140 A | 6/1987 | Sparks et al. | |
| 4,722,941 A | 2/1988 | Eckert et al. | |
| 4,861,598 A | 8/1989 | Oshlack | |
| 4,869,904 A | 9/1989 | Uekama et al. | |
| 5,190,947 A | 3/1993 | Riess et al. | |
| 5,356,467 A | 10/1994 | Oshlack et al. | |
| 5,460,826 A | 10/1995 | Merrill et al. | |
| 5,508,042 A | 4/1996 | Oshlack et al. | |
| 5,639,476 A | 6/1997 | Oshlack et al. | |
| 5,656,295 A | 8/1997 | Oshlack et al. | |
| 5,700,410 A | 12/1997 | Nakamichi et al. | |
| 5,756,123 A | 5/1998 | Yamamoto et al. | |
| 5,756,483 A | 5/1998 | Merkus | |
| 5,849,240 A | 12/1998 | Miller et al. | |
| 5,866,161 A | 2/1999 | Childers et al. | |
| 5,891,471 A | 4/1999 | Miller et al. | |
| 5,914,129 A | 6/1999 | Mauskop | |
| 5,952,005 A | 9/1999 | Olsson et al. | |
| 5,958,452 A | 9/1999 | Oshlack et al. | |
| 5,958,459 A | 9/1999 | Chasin et al. | |
| 5,965,161 A | 10/1999 | Oshlack et al. | |
| 5,965,163 A | 10/1999 | Miller et al. | |
| 5,968,551 A | 10/1999 | Oshlack et al. | |
| 6,048,736 A | 4/2000 | Kosak | |
| 6,068,855 A | 5/2000 | Leslie et al. | |
| 6,103,261 A | 8/2000 | Chasin et al. | |
| 6,156,764 A | 12/2000 | Asmussen et al. | |
| 6,162,467 A | 12/2000 | Miller et al. | |
| 6,248,363 B1 | 6/2001 | Patel et al. | |
| 6,255,502 B1 | 7/2001 | Penkler et al. | |
| 6,261,599 B1 | 7/2001 | Oshlack et al. | |
| 6,277,384 B1 | 8/2001 | Kaiko et al. | |
| 6,290,990 B1 | 9/2001 | Grabowski et al. | |
| 6,294,195 B1 | 9/2001 | Oshlack et al. | |
| 6,309,668 B1 | 10/2001 | Bastin et al. | |
| 6,310,072 B1 | 10/2001 | Smith et al. | |
| 6,328,979 B1 | 12/2001 | Yamashita et al. | |
| 6,335,033 B2 | 1/2002 | Oshlack et al. | |
| 6,375,957 B1 | 4/2002 | Kaiko et al. | |
| 6,379,707 B2 | 4/2002 | Vladyka, Jr. et al. | |
| 6,475,494 B2 | 11/2002 | Kaiko et al. | |
| 6,692,767 B2 | 2/2004 | Burnside et al. | |
| 6,696,088 B2 | 2/2004 | Oshlack et al. | |
| 6,706,281 B2 | 3/2004 | Oshlack et al. | |
| 6,723,343 B2 | 4/2004 | Kugelmann | |
| 6,743,442 B2 | 6/2004 | Oshlack et al. | |
| 6,919,372 B1 | 7/2005 | Yamashita et al. | |
| 7,011,846 B2 | 3/2006 | Shojaei et al. | |
| 7,261,529 B2 | 8/2007 | Persyn et al. | |
| 7,399,488 B2 | 7/2008 | Hirsh et al. | |
| 7,670,612 B2 | 3/2010 | Miller | |
| 7,771,707 B2 | 8/2010 | Hirsh et al. | |
| 8,449,909 B2 | 5/2013 | Hirsh et al. | |
| 8,557,291 B2 | 10/2013 | Rariy et al. | |
| 8,758,813 B2 | 6/2014 | Hirsh et al. | |
| 8,840,928 B2 | 9/2014 | Rariy et al. | |
| 9,044,398 B2 | 6/2015 | Hirsh et al. | |
| 9,248,195 B2 | 2/2016 | Rariy et al. | |
| 9,592,200 B2 | 3/2017 | Rariy et al. | |
| 9,682,075 B2* | 6/2017 | Rariy | A61K 31/485 |
| 9,737,530 B1* | 8/2017 | Saim | A61K 31/485 |
| 9,763,883 B2* | 9/2017 | Hirsh | A61K 9/1617 |
| 2001/0006650 A1 | 7/2001 | Burnside et al. | |
| 2001/0036476 A1 | 11/2001 | Oshlack et al. | |
| 2002/0032166 A1 | 3/2002 | Shefter et al. | |
| 2002/0081333 A1 | 6/2002 | Oshlack et al. | |
| 2003/0059397 A1 | 3/2003 | Hughes | |
| 2003/0064099 A1 | 4/2003 | Oshlack et al. | |
| 2004/0052731 A1 | 3/2004 | Hirsh et al. | |
| 2004/0062778 A1 | 4/2004 | Shefer et al. | |
| 2004/0170680 A1 | 9/2004 | Oshlack et al. | |
| 2005/0013862 A1 | 1/2005 | Tobyn et al. | |
| 2005/0181050 A1 | 8/2005 | Hirsh et al. | |
| 2005/0281748 A1 | 12/2005 | Hirsh et al. | |
| 2006/0104909 A1 | 5/2006 | Vaghefi et al. | |
| 2006/0110457 A1 | 5/2006 | Labrecque et al. | |
| 2007/0054002 A1 | 3/2007 | Persyn et al. | |
| 2008/0199530 A1 | 8/2008 | Hirsh et al. | |
| 2008/0260819 A1 | 10/2008 | Fleming et al. | |
| 2009/0142378 A1 | 6/2009 | Frisbee | |
| 2009/0297617 A1 | 12/2009 | Rariy et al. | |
| 2010/0260834 A1 | 10/2010 | Hirsh et al. | |
| 2011/0142943 A1 | 6/2011 | Rariy et al. | |
| 2013/0045960 A1 | 2/2013 | Hirsh et al. | |
| 2013/0310413 A1 | 11/2013 | Hirsh et al. | |
| 2014/0105987 A1 | 4/2014 | Rariy et al. | |
| 2014/0121232 A1 | 5/2014 | Hirsh et al. | |
| 2015/0004244 A1 | 1/2015 | Rariy et al. | |
| 2015/0005332 A1 | 1/2015 | Rariy et al. | |
| 2015/0265596 A1 | 9/2015 | Hirsh et al. | |
| 2016/0074326 A1 | 3/2016 | Rariy et al. | |
| 2017/0182032 A1 | 6/2017 | Rariy et al. | |
| 2017/0360710 A1 | 12/2017 | Hirsh et al. | |
| 2017/0368057 A1 | 12/2017 | Saim et al. | |

FOREIGN PATENT DOCUMENTS

| | | |
|---|---|---|
| EP | 0253104 A1 | 1/1988 |
| EP | 0375063 A1 | 6/1990 |
| EP | 0578231 A1 | 1/1994 |
| EP | 0647448 A1 | 4/1995 |
| GB | 1513166 | 6/1978 |
| WO | WO 93/10765 A1 | 6/1993 |
| WO | WO 95/20947 A1 | 8/1995 |
| WO | WO 97/14438 A1 | 4/1997 |
| WO | WO 97/49402 A1 | 12/1997 |
| WO | WO 1998/002187 A1 | 1/1998 |
| WO | WO 98/18827 A1 | 5/1998 |
| WO | WO 1999/001111 A1 | 1/1999 |
| WO | WO 1999/042086 A1 | 8/1999 |

(56) References Cited

FOREIGN PATENT DOCUMENTS

| WO | WO 00/50007 A1 | 8/2000 |
| WO | WO 01/08661 A2 | 2/2001 |
| WO | WO 01/58447 A1 | 8/2001 |
| WO | WO 01/72338 A1 | 10/2001 |
| WO | WO 2002/013786 A2 | 2/2002 |
| WO | WO 03/004029 A1 | 1/2003 |
| WO | WO 2004/004693 A1 | 1/2004 |
| WO | WO 2004/075877 A1 | 9/2004 |
| WO | WO 2005/123039 A1 | 12/2005 |

OTHER PUBLICATIONS

"International Preliminary Report on Patentability," 3 pages, PCT appl. No. PCT/US03/21095 (dated Apr. 25, 2005).
"International Preliminary Report on Patentability," 6 pages, PCT appl. No. PCT/US2005/020588 (dated Oct. 2, 2006).
"International Search Report," 2 pages, PCT appl. No. PCT/US03/21095 (dated Nov. 6, 2003).
"International Search Report," 4 pages, PCT appl. No. PCT/US2005/020588 (dated Sep. 9, 2005).
"International Search Report," 2 pages, PCT appl. No. PCT/US2016/050092 (dated Nov. 22, 2016).
"Supplementary European Search Report," 7 pages, EP appl. No. 03763229.6 (dated Sep. 19, 2008).
"Written Opinion of the International Searching Authority," 6 pages, PCT appl. No. PCT/US2005/020588 (dated Sep. 9, 2005).
"Written Opinion," 4 pages, PCT appl. No. PCT/US03/21095 (dated Jun. 20, 2004).
"Written Opinion of the International Searching Authority," 7 pages, PCT appl. No. PCT/US2016/050092 (dated Nov. 22, 2016).
Abuse and Mental Health Services Administration, "Results from the 2004 National Survey on Drug Use and Health: National Findings," pp. 1-310 (2005).
Buist et al., "Four salt phases of theophylline," Struct. Chem. Acta Crystal. Sect. C C70:220-224 (2014).
Bush et al., "A comparison of a theophylline-ephedrine combination with terbutaline " Ann. Allergy 41:13-17 (1978) abstract.
Chemical Abstract Society (CAS), Properties for HPMC (CAS reg. No. 9004-65-3) accessed Jun. 29, 2013.
Choi et al., "Hydrophobic ion pair formation between leuprolide and sodium oleate for sustained release from biodegradable polymeric microspheres," Int. J. Pharm. 203:193-202 (2000).
Cortesi, et al., "Sugar cross-linked gelatin for controlled release: microspheres and disks," Biomaterials 19:1641-1649 (1998).
Gennaro, ed., Remington: The Science and Practice of Pharmacology, 20th ed., Lippincott: Baltimore, MD, pp. 704-706 (2000).
Lan et al., "Studies on the Synthesis and Thermal Properties of Copoly(L-lactic acid/glycolic acid) by Direct Melt Polycondensation," J. Appl. Polymer Sci. 92:2163-2168 (2004).
Nakamura, et al., "Development of an oral sustained release drug delivery system utilizing pH-dependent swelling of carboxyvinyl polymer", J. Control. Rel., 111:309-315 (2006).
Ozturk et al., "Mechanism of Release from Pellets Coated with an Ethylcellulose-Based Film," J. Control. Rel. 14:203-213 (1990).
Raffin et al., "Sodium pantoprazole-loaded enteric microparticles prepared by spray drying: Effect of the scale of production and process validation," Int. J. Pharm. 324:10-18 (2006).
Redden et al., "In vitro hydrolysis of polyunsaturated fatty acid N-acyloxymethyl derivatives of theophylline," Int. J. Pharm. 165:87-96 (1998).
Rodriguez et al., "Description and preliminary evaluation of a new ultrasonic atomizer for spray-congealing processes," Int. J. Pharm. 183(2):133-143 (1999).
Takka et al., "Effect of anionic polymers on the release of propanol hydrochloride from matrix tablets," Eur. J. Pharm. Biopharm. 52:75-82 (2001).
U.S. Department of Health and Human Services et al., "Abuse-Deterrent Opioids—Evaluation and Labeling. Guidance for Industry," http://www.fda.gov/Drugs/GuidanceComplianceRegulatoryInformation/Guidances/default.htm, 29 pages (Apr. 2015).
Yow et al., "Combined Streptomycin and Erythromycin Therapy in Subacute Bacterial Endocarditis," Am. J. Med. 16(4):613 (Apr. 1954).
Kim and Pack, Microspheres for Drug Delivery, in BioMEMS and Biomedical/Nanotechnology, pp. 19-50, Springer US (2006), 34 pages.
Toxicological Evaluation of Some Food Colours, Emulsifiers, Stabilizers, Anti-Caking Agents and Certain Other Substances FAO Nutrition Meetings Report Series No. 46A WHO/FOOD ADD/70.36, Report on Deliberations of the Joint FAO/WHO Expert Committee on Food Additives, Rome, May 27-Jun. 4, 1969 ("FAO/WHO report"), 162 pages.
Leuner and Dressman, "Improving drug solubility for oral delivery using solid dispersions." European Journal of Pharmaceutics and Biopharmaceutics (2000); 50(1): 47-60.
Guidance for Industry Q1A(R2) Stability Testing of New Drug Substances and Products, U.S. Department of Health and Human Services Food and Drug Administration, Center for Drug Evaluation and Research (CDER), Center for Biologics Evaluation and Research (CBER) ("FDA Guidance"), Nov. 2003, ICH, Revision 2, 25 pages.
Emås and Nyqvist, "Methods of studying aging and stabilization of spray-congealed solid dispersions with carnauba wax." International Journal of Pharmaceutics (2000); 197(1-2): 117-127, 13 pages.
Pöyhia, et al., "The pharmacokinetics and metabolism of oxycodone after intramuscular and oral administration to healthy subjects." British Journal of Clinical Pharmacology (1992); 33(6): 617-621.
Handbook of Pharmaceutical Excipients, 2nd ed., (eds. Wade and Weller), American Pharmaceutical Association (1994), pp. 82-83, 325-328, 544-545; 552-553; and 558-561, 16 pages.
Gandhi, et al., "Extrusion and spheronization in the development of oral controlled-release dosage forms." Pharmaceutical Science & Technology Today (1999); 2(4): 160-170.
Berkland, et al., "Fabrication of PLG microspheres with precisely controlled and monodisperse size distributions." Journal of Controlled Release (2001); 73(1): 59-74.
Choi, et al., "Effect of polymer molecular weight on nanocomminution of poorly soluble drug." Drug Delivery (2008); 15(5): 347-353.
Murthy and Ghebre-Sellassie, "Current perspectives on the dissolution stability of solid oral dosage forms." Journal of Pharmaceutical Sciences (1993); 82(2): 113-126.
Hawley's Condensed Chemical Dictionary, 13th ed., John, Wiley & Sons, Inc., New York, 1997, p. 1178, defining "wax", 4 pages.
Meyer and Manning, "Hydrophobic Ion Pairing: Altering the Solubility Properties of Biomolecules." Pharmaceutical Research (1998); 15(2): 188-193.
Sjökvist, et al., "Physicochemical aspects of drug release. XIV. The effects of some ionic and non-ionic surfactants on properties of a sparingly soluble drug in solid dispersions." International Journal of Pharmaceutics (1992); 79(1-3): 123-133.

* cited by examiner

TAMPER-RESISTANT PHARMACEUTICAL COMPOSITIONS OF OPIOIDS AND OTHER DRUGS

CROSS REFERENCE TO RELATED APPLICATIONS

This application is a continuation of U.S. patent application Ser. No. 14/320,086, filed Jun. 30, 2014, which is a continuation of U.S. patent application Ser. No. 12/965,572, filed Dec. 10, 2010, now U.S. Pat. No. 8,840,928, which claims the benefit of U.S. Patent Appl. Ser. No. 61/285,231, filed Dec. 10, 2009, the disclosures of all of which are incorporated by reference as if fully set forth herein.

FIELD OF THE INVENTION

The present invention is generally in the field of pharmaceutical compositions, specifically compositions that are designed to reduce the potential for improper administration of drugs, such as those subject to abuse and methods of making thereof.

BACKGROUND OF THE INVENTION

Oxycodone, morphine, and other opioid analgesics are successful and therapeutically useful medications, e.g., as pain killers, when administered orally. Unfortunately, they also pose a severe threat for willful abuse due to their ability to alter mood and/or cause a sense of euphoria. Traditional sustained release formulations of such drugs, which contain a relatively large amount of drug meant to be released from the formulation over an sustained time period, are particularly attractive to abusers since the sustained release action can be destroyed by crushing or grinding the formulation. The resulting material (i.e., the crushed formulation) can no longer control the release of drug. Depending on the drug, abusers can then (1) snort the material, (2) swallow the material or (3) dissolve the material in water and subsequently inject it intravenously. The dose of drug contained in the formulation is absorbed immediately through the nasal or GI mucosa (e.g., snorting or swallowing, respectively) or is administered in a bolus to the systemic circulation (e.g., IV injection). These abuse methods result in the rapid bioavailability of relatively high doses of drug, giving the abuser a "high". Since relatively simple methods (crushing, grinding, chewing and/or dissolution in water) can be used to transform such formulations into an abusable form, they provide virtually no deterrent to a potential abuser.

For example, in recent years, there have been numerous reports of diversion and abuse of sustained release formulations of opioids such as oxycodone, oxymorphone and morphine. According to a report from the Abuse and Mental Health Services Administration, results from the 2007 National Survey on Drug use and Health: National Findings (Rockville, Md.; US Dept. of Health and Human Services), showed that in both 2006 and 2007, an estimated 5.2 million persons aged 12 or older (2.1 percent in each year) were current nonmedical users of prescription pain relievers. Additionally, from 2002 to 2007, there was an increase among young adults aged 18 to 25 in the rate of current use of prescription pain relievers, from 4.1 to 4.6 percent. Data from this survey also supports the notion that sustained-release formulations susceptible to tampering methods such as chewing, crushing and grinding likely contributes to the increasing rates of prescription pain reliever abuse. For example, in 2007, there were an estimated 54,000 new nonmedical users of OxyContin® (a sustained release formulation of the active drug oxycodone).

Oxycodone is a controlled substance in Schedule II of the Controlled Substances Act (CSA), which is administered by the Drug Enforcement Administration (DEA). Despite the fact that Schedule II provides the maximum amount of control possible under the CSA for approved drug products, in practice it is difficult for law enforcement agencies to control the diversion or misuse of legitimate prescriptions. Although abuse, misuse, and diversion are potential problems for all opioids, including Oxycodone, opioids are very important part of the medical armamentarium for the management of pain when used appropriately under the careful supervision of a physician.

U.S. Pat. No. 3,980,766 to Shaw et al. ("Shaw"), U.S. Pat. No. 4,070,494 to Hoffmeister et al. ("Hoffmeister"), and U.S. Pat. No. 6,309,668 to Bastin et al. ("Bastin") describe formulations designed to prevent the injection of compositions meant for oral administration.

Shaw describes the incorporation of an ingestible solid which causes a rapid increase in viscosity upon concentration of an aqueous solution thereof.

Hoffmeister describes the incorporation of a non-toxic, water gelable material in an amount sufficient to render the drug resistant to aqueous extraction.

Bastin describes a tablet for oral administration containing two or more layers containing one or more drugs and one or more gelling agents within separate layers of the tablet. The resulting tablet forms a gel when combined with the volume of water necessary to dissolve the drug allegedly reducing the extractability of the drug from the tablet.

It should be noted that although these compositions allegedly preclude abuse by injection, this approach fails to prohibit dissolution of the drug once the dosage form is crushed into smaller particles or pieces. Thus, these formulations are vulnerable to abuse by crushing and swallowing or snorting the formulation, which are commonly reported methods of abuse.

U.S. Pat Nos. 3,773,955 and 3,966,940 to Pachter et al. describe formulations containing a combination of opioid agonists and antagonists, in which the antagonist does not block the therapeutic effect when the admixture is administered orally, but which does not produce analgesia, euphoria or physical dependence when administered parenterally by an abuser.

U.S. Pat. No. 4,457,933 to Gordon et al. describes a method for decreasing both the oral and parenteral abuse potential of strong analgetic agents by combining an analgesic dose of the analgetic agent with an antagonist in specific, relatively narrow ratios.

U.S. Pat. Nos. 6,277,384, 6,375,957 and 6,475,494 to Kaiko et al. describe oral dosage forms including a combination of an orally active opioid agonist and an orally active opioid antagonist in a ratio that, when delivered orally, is analgesically effective but that is aversive in a physically dependent subject. While such a formulation may be successful in deterring abuse, it also has the potential to produce adverse effects in legitimate patients.

The FDA recently approved two sustained release formulations of opioid active ingredients with tamper resistant features. A sustained release oxycodone tablet, designed to resist crushing and to get in the presence of water, is currently available. Also a multiparticulate-in-capsule product containing morphine and a sequestered naltrexone is also commercially available; this product is designed to release naltrexone (an opioid antagonist) to counteract the euphoric effects of the opioid active ingredient when the formulation is crushed, chewed or dissolved. While such formulations offer an improvement over previously available formulations with respect to susceptibility to tampering, there are disadvantages associated with the available products. For example, tablet formulations that are difficult to crush, but not crush-proof, can still be chopped or shredded into small particles and do not address the needs of patients with difficulty swallowing, and formulations containing antagonists have the potential to cause harm to legitimate patients.

It is therefore an object of the present invention to provide a pharmaceutical composition (e.g., a multiparticulate composition) that reduces the potential for improper administration of drugs without the addition of aversive agents or antagonists, which have the potential to cause harm to legitimate patients. Such a formulation significantly reduces the potential for improper administration or use of drugs but, when administered as directed, is capable of delivering a therapeutically effective dose. Methods of making and using such a formulation are also provided.

SUMMARY OF THE INVENTION

An abuse-deterrent pharmaceutical composition and methods of making and using thereof have been developed. The compositions can be used to reduce the likelihood of improper administration of drugs, especially drugs prone to abuse such as oxycodone. The technology is useful for a number of other drugs were sustained release oral delivery is desired, and there is potential for abuse if the drug dose is made immediately available for nasal, intravenous (IV) or oral administration. In a preferred embodiment, the drug is formulated into multiparticulates containing lipophilic or water-insoluble materials. In some embodiments, the drug is modified to increase its lipophilicity prior to or during the formulation of the multiparticulates. For example, the composition is formulated with one or more excipients that interact ionically with the drug to obtain a more lipophilic drug derivative. The composition is then formulated as multiparticulates. In another embodiment, the multiparticulates are produced using a spray congealing process. In other embodiments, the formulation contains lipophilic or water-insoluble materials or is made using a process which increases the lipophilicity and/or water-insolubility of the composition. In some embodiments, the composition additionally contains one or more antioxidants, surfactants, or polymers.

The abuse-deterrent composition retards the release of drug even if the physical integrity of the dosage form is compromised (for example, by chopping with a blade or crushing) and the resulting material is placed in water, snorted, or swallowed. However, when administered as directed, the drug is released slowly, typically over a period of 6-24 hours, from the composition as the composition is broken down or dissolved gradually within the GI tract by a combination of surfactant action of bile acids, diffusion, mechanical erosion and, in some embodiments, enzymatic degradation.

The multiparticulates or microparticulates described herein can be made using a variety of technique known in the art including, but not limited to, spray congealing, spray chilling, extrusion, spray drying, and bulk congealing with subsequent milling. In one embodiment, beads or particles containing the active agent (e.g., a fatty acid salt of the active agent) and excipients are prepared using a spray congealing process.

In one embodiment, the multiparticulates have a D(0.1) particle size from about 50 to about 250 µm, preferably from about 140 to about 190 µm; a D(0.5) median particle size from about 150 to about 750 µm, preferably from about 200 to about 400 µm; and a D(0.9) particle size from about 200 to about 1200 µm, preferably from about 400 to about 700 µm. The multiparticulates are characterized by a span (i.e., [D(0.9)-D(0.1)]/D(0.5)) less than 5, preferably less than 2, and more preferably less than 1.4. In some embodiments, multiparticulates having a span of less than 1.4 are less prone to segregation during processing and/or achieve the desired pharmacokinetic profile. D(0.1), D(0.5) and D(0.9) are defined as the diameters where 0%, 50%, or 90% w/w of the multiparticulates have a smaller diameter, respectively, when measured, e.g., using a later diffraction technique. The terms "D(0.5)" and "median particle size" are used interchangeably herein. The multiparticulates can be any geometrical shape. In some embodiments, the multiparticulates may be irregular, oblong or spherical in shape. In a preferred embodiment, the multiparticulates are substantially round or spherical in shape (e.g., beads).

In another embodiment, the beads have a D(0.5) median particle size from about 150 to about 750 µm, preferably from about 250 to about 400 µm.

In some embodiments, the individual drug-containing multiparticulates are coated with one or more independent coating layers. At least one of the coating materials is water-insoluble and/or organic solvent-insoluble, so that in vitro dissolution of the formulation will require more than one step. Thus, the drug is not easily extractable from the formulations by conventional chemical means. In contrast, when administered to the gastrointestinal tract via swallowing, the drug will gradually break down of the formulation via surfactant action of bile acids; mechanical erosion and, in some embodiments, enzymatic degradation. The particles can be coated using a variety of techniques known in the art including, but not limited to, wet granulation processes, spray coating processes, and/or coacervation processes.

The pharmaceutical composition, when administered orally, results in a desired drug release profile. The release profile provides a therapeutic effect for an extended period of time, typically from 6 to 24 hours, preferably from 12 to 24 hours. Additional compositions may achieve a small immediate release dose that precedes the extended release of drug. The compositions disclosed herein may optionally contain a drug having no appreciable abuse potential.

DETAILED DESCRIPTION OF THE INVENTION

Figure 1:
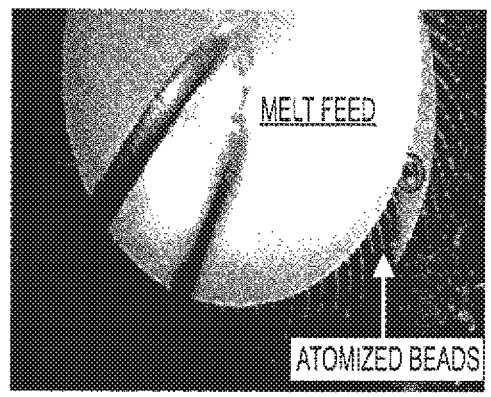
FIG. 1 is a picture of a portion of a spinning disc atomizer.

Disclosed herein are abuse-deterrent pharmaceutical compositions and the method of making and using the compositions.

1. Compositions

As used herein, "composition" refers to the drug dosage unit for administration to a patient. "Composition" may also be used in reference solely to the active ingredient, or to a formulation containing the active ingredient.

The currently available extended release dosage forms containing narcotic analgesics and other drugs are subject to misuse, in part, because mechanical destruction of the dosage form exposes the encapsulated drug and allows for rapid dissolution of the drug into aqueous media. Three properties of the dosage form that contribute to this outcome are, (1) the high water solubility of the drug salt form; (2) the lack of protection offered by the hydrophilic and/or water soluble excipients in the formulation; and (3) the ease with which the surface area of the formulation is increased by simple chewing or crushing. Susceptibility to simple methods such as chewing or crushing is particularly problematic for monolithic controlled-release dosage forms. For monolithic dosage forms, such as tablets, even splitting the unit into a few pieces (without completely crushing it) can result in a dramatic increase in the dissolution rate.

In the compositions disclosed herein, one or more of these properties are altered in order to achieve an abuse-deterrent composition. Specifically, in the one embodiment, the drug is modified to increase its lipophilicity and reduce its water solubility. The modified drug is homogeneously dispersed within one or more excipients that are either slowly soluble or not soluble in water. Dispersion within these materials further reduces the accessibility of the when crushed and exposed to an aqueous media. In some embodiments, the drug may be partially or fully dispersed in the excipients on a molecular level. The intimate mixture of modified drug and excipients is subsequently formulated into multiparticulates, producing a formulation whose surface area is minimally influenced by chewing or crushing.

The terms "tamper resistant formulation," "abuse-deterrent composition" or "abuse-deterrent formulation" are used interchangeably herein to refer to compositions that reduce the potential for improper administration of drugs but that deliver a therapeutically effective dose when administered as directed. Improper administration includes tampering with the dosage form and/or administering the drug by any route other than instructed. For example, for a tablet or capsule, methods of tampering with the dosage form may include, but are not limited to, breaking, crushing, grinding, chewing and/or dissolving the tablet or the contents of the capsule. For oral administration, improper administration includes administering the drug by any route other than via swallowing.

The abuse deterrent compositions preferably contain a drug modified to increase its lipophilicity. In some embodiments, the drug is homogeneously dispersed within multiparticulates composed of a material that is either slowly soluble in water or water insoluble. The compositions maintain a slow release of drug if the dosage form is chopped or crushed and the resulting material is placed in water, snorted, or swallowed since most of the drug will remain associated with or entrapped within portions of the core material of the composition. In other embodiments, the drug containing multiparticulates are coated with one or more coating layers, where at least one coating is water insoluble and/or organic solvent insoluble. The components of the resulting coated multiparticulates are not mutually soluble in water or organic solvents. Therefore, extraction of the drug from the formulation cannot be carried out in one step. However, when administered as directed, the drug is slowly released from the formulation via diffusion and erosion within the environment of the gastrointestinal tract.

A. Drugs to be Formulated

There are many drugs which can be delivered using the compositions described herein. The Controlled Substances Act (CSA), Title II of the Comprehensive Drug Abuse Prevention and Control Act of 1970, places all substances that are regulated under existing federal law into one of five schedules based upon the substance's medicinal value, harmfulness, and potential for abuse or addition. Drugs that are preferred include those classified as Schedule II, III, IV and V drugs. Drugs that are most preferable include those, like oxycodone, that are currently formulated as extended or controlled release composition, where drug release is intended to occur over a prolonged period of time through the gastrointestinal tract, and immediate or burst release, for example, by inhalation or injection, is undesirable. As used herein, drugs prone to abuse refer to controlled substance specified as schedule II, III, IV and V drugs. Other opioid analgesics that can be incorporated into the compositions described herein include morphine and hydromorphone.

The terms "drug", "active agent", and "pharmaceutically active agent" are used interchangeably hereinto refer to a chemical compound that induces a desired pharmacological, physiological effect. The terms also encompass pharmaceutically acceptable derivatives of those active agents specifically mentioned herein, including, but not limited to, salts, solvates, hydrates, complexes with one or more molecules, prodrugs, active metabolites, and derivative and analogs. When the terms "active agent", "pharmacologically active agent" and "drug" are used, or when a particular drug, such as oxycodone, is identified, it is to be understood as including the active agent per se as well as pharmaceutically acceptable salts, solvates, hydrates, complexes with one or more molecules, prodrugs, active metabolites, and analogs.

Examples of preferred drugs include 1-phenylcyclohexylamine, 1-piperidinocyclohexanecarbonitrile, alfentanil, alphacetylmethadol, alphaprodine, alprazolam, amobarbital, amphetamine, anileridine, apomorphine, aprobarbital, barbital, barbituric acid derivative, bemidone, benzoylecgonine, benzphetamine, betacetylmethadol, betaprodine, bezitramide, bromoazepam, buprenorphine, butabarbital, butalbital, butorphanol, camazepam, cathine, chloral, chlordiazepoxide, clobazam, clonazepam, clorazepate, clotiazepam, cloxazolam, cocaine, codeine, chlorphentermine, delorazepam, dexfenfluramine, dextromoramide, dextropropoxyphen, dezocine, diazepam, diethylpropion, difenoxin, dihydrocodeine, dihydromorphine, dioxaphentyl butyrate, dipanone, diphenoxylate, diprenorphine, ecogonine, enadoline, eptazocine, estazolam, ethoheptazine, ethyl loflazepate, ethylmorphine, etorphine, femproponex, fencamfamin, fenfluramine, fentanyl, fludiazepam, flunitrazepam, flurazepam, glutethimide, halazepam, haloxazolam, hexalgon, hydrocodone, hydromorphone, isomethadone, hydrocodone, ketamine, ketazolam, ketobemidone, levanone, levoalphacetylmethanol, levomethadone, levomethadyl acetate, levomethorphan, levorphanol, lofentanil, loperamide, loprazolam, lorazepam, lormetazepam, lysergic acid, lysergic acid amide, mazindol, medazepam, mefenorex, meperidine, meptazinol, metazocine, methadone, methamphetamine, methohexital, methotrimeprazine, methyldihydromorphinone, methylphenidate, methylphenobarbital, metopon, morphine, nabilone, nalbuphine, nalbupine, nalorphine, narceine, netopam, nicomorphine, nimetazepam, nitrazepam, nordiazepam, normethadone, normorphine, oxazepam, oxazolam, oxycodone, oxymorphone, pentazocine, pentobarbital, phenadoxone, phenazocine, phencyclidine, phendimetrazine, phenmetrazine, pheneridine, piminodine, prodilidine, properidine, propoxyphene, racemethorphan, racemorphan, racemoramide, remifentanil, secobarbital, sufentanil, talbutal, thebaine, thiamylal, thiopental, tramadol, trimeperidine, and vinbarbital.

In addition to the compounds above, the following scheduled drugs may be incorporated into the composition: allobarbitone, alprazolam, amylobarbitone, aprobarbital, barbital, barbitone, benzphetamine, brallobarbital, bromazepam, brotizolam, buspirone, butalbital, butobarbitone, butorphanol, carmazepam, captodiame, carbromal, carfentamil, carpiprathine, cathine, chloral, chloral betaine, chloral hydrate, chloralose, chlordiazepoxide, chlorhexadol, chlormethiazole, edisylate, chlormezanone, cinolazepam, clobazam, potassium clorazepate, clotiazepam, cloxazolam, cyclobarbitone, delorazepam, dexfenfluramine, diazepam, diethylpropion, difebarbamate, difenoxin, enciprazine, estazolam, ethyl loflazepate, etizolam, febarbamate, fencamfamin, fenfluramine, fenproporex, fluanisone, fludiazepam, fluniraam, flunitrazepam, flurazepam, flutoprazepam, gepirone, glutethimide, halazepam, haloxazolam, bexobarbitone, ibomal, ipsapirone, ketazolam, loprazolam mesylate, lorazepam, lormetazepam, mazindol, mebutamate, medazepam, mefenorex, mephobarbital, meprobamate, metaclazepam, methaquadone, methohexital, methylpentynol, methylphenobarbital, midazolam, milazolam, morphine, nimetazepam, nitrazepam, nordiazepam, oxazepam, oxazolam, paraldehyde, pemoline, pentabarbitone, pentazocine, pentobarbital, phencyclidine, phenobarbital, phendimetrazine, phenmetrazine, phenprobamate, phentermine, phenyacetone, pinazepam, pipradol, prazepam, proxibarbal, quazepam, quinalbaritone, secobarbital, secbutobarbitone, sibotramine, temazepam, tetrazepam, triazolam, triclofos, zalepan, zaleplon, zolazepam, zolpidem, zopiclone.

Certain compounds described herein may exist in particular geometric or stereoisomeric forms. The composition disclosed herein contemplates all such compounds, including cis- and trans-isomers, R- and S-enantiomers, diastereomers, (d)-isomers, (l)-isomers, the racemic mixtures thereof, compounds of different spacial conformations, and other mixture thereof, as falling within the scope of the invention. Additional asymmetric carbon atoms may be present in a substituent such as an alkyl group. All such isomers, as well as mixtures thereof, are intended to be included in this invention.

As used herein, "pharmaceutically acceptable salts" refers to derivatives of the disclosed compounds wherein the parent compound is modified by making salts thereof. Pharmaceutically acceptable salts include salts of acidic (e.g., a carboxylic acid) or basic groups (e.g., a primary, secondary or tertiary amine) present in compounds disclosed herein. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salt of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, lauric, capric, myristic, palmitic, stearic, oleic, linoleic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, and isethionic.

The pharmaceutically acceptable salts of the compounds can be synthesized from the parent compound (e.g., the unprotonated base form of the compound, often referred to as the "free base" of the compound), which contains a basic or acidic moiety, by conventional chemical methods. Generally, such salt can be prepared by reacting the free acid or base forms of these compounds with the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704, the disclosure of which is hereby incorporated by reference.

Pharmaceutically acceptable salts may also be prepared by reacting the free acid or base forms of compounds with an appropriate base or acid, respectively, in a melt process, optionally in the presence of other pharmaceutically acceptable excipients (e.g., waxes). As used herein, the term "melt process" refers to a process where the free acid or base forms of the compounds are dissolved in one or more excipients that are in molten form (i.e., it is a solid at room temperature) to make a solution wherein the base or acid interacts with the free acid or base form of the compounds, respectively, to form the desired pharmaceutically acceptable salt.

Optionally, the composition described herein can further include a drug having no appreciable abuse potential.

B. Drug Modification

In some embodiments, the dissolution and/or solubility characteristics of a drug are altered. Modification of the drug to produce a more lipophilic and/or less soluble derivative serves to reduce the dissolution rate and/or solubility of the drug in aqueous media, such as water, and thus reduce the aqueous extractability of the drug. Furthermore, if the drug is made more lipophilic, it can be dissolved in a molten fatty substance and/or wax like mixture; that is, the more lipophilic form of the drug is substantially more soluble in the molten fatty substance and/or wax-like mixture, as opposed to being mostly suspended or dispersed as solid particles in the molten fatty substance and/or wax-like mixture. Solubilization of the drug in lipophilic excipients can enhance the abuse-deterrent properties of multiparticulates formulated from the mixture as it is more difficult to extract drug from an intimately dispersed composition. Furthermore, such a composition is capable of controlling the release of drug, even when formulated into relatively small multiparticulates. Microparticulate composition, in contrast to monolithic compositions, are inherently less susceptible to tampering by mechanisms such as chewing or crushing that are intended to increase the surface area and, consequently, the release rate of drug.

The terms "lipophilic derivative" and "lipophililic drug derivative", as used herein, refer to derivatives of the drug that are less soluble or dissolve less rapidly in water than more soluble salts of the drug; the more soluble salts being selected from either base addition salts (for acidic drugs) or acid addition salts (for basic drugs), such a by the addition of inorganic acids. The examples of the latter include but are not limited to hydrohalics, sulfates, and nitrates. In some embodiments, a "lipophilic derivative" or "lipophililic drug derivative", is formed when the drug interacts ionically with one or more organic excipients. Ionic interactions include, but are not limited to, interactions between ionic moieties on a drug (e.g., cationic moieties or amionic moieties) and one or more ionic components (e.g., cationic moieties or anionic moieties) contained in the one or more organic excipients. In some embodiments, ionic interactions include, but are not limited to, the formulation of salts. In other embodiments, ionic interactions include hydrogen-bonding interactions between basic drug and acids (e.g., a nitrogen atom on the drug and the hydrogen atom on the carboxylic acid of the fatty acid) or acidic drugs and bases (e.g., a carboxylic acid hydrogen atom and the nitrogen atom of the fatty amine). As used herein, the term "fatty amine" includes, but is not limited to, $C_5$-$C_{30}$ fatty amines including octyl amine, decylamine, dodecylamine, tetradecylamine, hexadecylamide, octadecylamine, and palmitylamine.

Exemplary methods that can be used to alter the drug's lipophilicity and/or aqueous solubility are described below. It is understood that two or more approaches can be combined to achieve a desired dissolution and/or solubility profile.

In one embodiment, the drug's lipophilicity/solubility is modified by forming an ionic interaction (e.g., forming a salt) between a drug molecule and a charged lipophilic compound. In this case the lipophilicity of the resulting salt can be manipulated by varying the lipophilicity of the counter-ion. In general, lipophilic acids or amine with chain lengths between $C_5$-$C_{30}$ are lipophilic counter-ion candidates. Some specific examples include, but are not limited to, linoleic acid, octanoic acid, capric acid, lauric acid, myritic acid, palmitic acid, stearic acid, oleic acid, octyl amine, lauryl amine, stearyl amine, palmityl amine, linoleyl amine, and oleyl amine.

The formulation of an ionic interaction (e.g., forming a salt) between a pharmaceutically active agent and an excipient such as a fatty acid or amine can be accomplished by a melt process, with or without the use of a solvent. In some embodiments, one or more fatty acids or amines are heated above their melting point and the pharmaceutically active agent, in free base or acid form, is added to the molten fatty acid or amine either directly or after dissolution of the active agent in an appropriate solvent, such as ethanol or methylene chloride. When the active agent interacts ionically with the fatty acid or fatty amine the interaction can be such that, e.g., the fatty acid protonates a protonatable moiety on the active agent (e.g., a primary, secondary or tertiary amine) thereby placing a charge on the moiety and generating an ionized moiety (e.g., a protonated amine or ammonium moiety) on the active agent. The ionized moiety, in turn, interacts with the carboxylate ion of the fatty acid, which is itself ionized. In some embodiments, the interaction between the ionized moiety of the active agent and the carboxylate ion of the fatty acid can be intimate (e.g., an intimate ion pair), it can be separated by solvent or it an be separated by one or more excipient molecules. The fatty acids or amines are present, preferably, in an amount one to fifteen times the molar amount of the pharmaceutically active agent, more preferably, two to ten times the molar amount of the pharmaceutically active agent. The mass of fatty acid or amine required to dissolves the active agent is a function of the chain length of the fatty acid or amine. Some factors determining the amount of fatty acid or amine required to dissolve a given amount of active agent include but are not limited to base strength, acid strength, steric hindrance, and the ability of the active agent to for non-covalent interactions with the fatty acid or fatty amine (e.g., hydrogen bonding).

Other salts of the pharmaceutically active agent, which are contemplated by the present invention in order to alter the solubility and/or dissolution rate relative to the parent drug compound (e.g., the free acid or free base form of the compound) include, but are not limited to, pectinate, tannate, phytate, salicylate, saccharinate, acesulfumate, gallate, and terephthalate salts.

In some embodiments, salts of the pharmaceutically active agent, which are contemplated by the present invention, include those salts where the counter-ion is polymeric in nature. For example, anionic copolymers based on methacrylic acid and methyl methacrylate sold under the trade name Eudragit (e.g., Eudragit L100 and Eudragit (S100), acrylic acid polymers, and crosslinked acrylic acid polymers may be used to form a salt with drug molecules. Naturally occurring polymers and their derivatives, for example, carboxymethylcellulose, may also be used to form a salt with the drug molecules. In the cases of polymeric counter-ions, the number of drug molecules reacted with the polymer to form a salt may or may not be equimolar with respect to the number of salt-forming sites on the polymer chain.

In another embodiment, a drug is covalently modified to increase its lipophilicity. For example, a lipophilic compound can be covalently attached to a drug molecule via an ester or amide linkage. Such drug derivatives are cleaved in vivo, thus releasing the parent compound.

In one embodiment, the drug is made more lipophilic by eliminating or reducing the overall charge of the drug molecule. For example, for a basic drug, a water soluble salt (such as hydrochloride, sulfate, or maleate) can be converted to a free base using techniques known in the art. In the case of an acidic drug, a water soluble salt (such as sodium, potassium, or the like) can be converted to a free acid.

C. Drug Containing Multiparticulates

In some embodiments, the drug is formulated with one or more excipients to form multiparticulates. As used herein, the terms "multiparticulate," "particle", "microparticle," and "bead," which are used interchangeably, refer to a composition containing a drug dispersed within one or more excipients. The terms "coated multiparticulate" and "coated microparticle," which are used interchangeably, refer to a composition containing a drug containing multiparticulate coated with one or more coating layers of material. Multiparticulates and coated multiparticulates have a size of from about 1 to about 3000 microns in diameter, for example, from about 10 to about 3000 microns, from about 100 to about 1000 microns, from about 500 to about 2000 microns, from about 1000 to about 3000 microns, from about 500 to about 1500 microns or from about 1 to about 1000 microns.

In one embodiment, the multiparticulates have a D(0.1) particle size from about 50 to about 250 μm, preferably from about 140 to about 190 μm; a D(0.5) median particle size from about 150 to about 750 μm, preferably from about 200 to about 400 μm; and a D(0.9) particle size from about 200 to about 1200 μm, preferably from about 400 to about 700 μm. The multiparticulates are characterized by a span (i.e., [D(0.9)-D(0.1)]/D(0.5)) less than 5, preferably less than 2, and more preferably less than 1.4. In some embodiments, multiparticulates having a span of less than 1.4 are less prone to segregation during processing and/or are more likely to achieve the desired pharmacokinetic profile. D(0.1), D(0.5) and D(0.9) are defined as the diameters were 10%, 50% or 90% w/w of the microparticles have a smaller diameter, respectively, when measured, e.g., using a laser diffraction technique. The multiparticulates can be any geometrical shape. In some embodiments, the multiparticulates may be irregular, oblong or spherical in shape. In a preferred embodiment, the multiparticulates re substantially round or spherical in shape (e.g., beads).

In another embodiment, the beads have a D(0.5) median particle size from about 150 to about 750 µm, preferably from about 250 to about 400 µm.

The term "solid dispersion" is defined as a system having small particles of drug, typically of less than 400 µm in size, more typically less than 100 µm in size, and most typically less than 10 µm in size, of one phase dispersed in another phase (the carrier phase). The term "solid solution" is defined as a system in a solid state wherein the drug is molecularly dispersed throughout a matrix such that the system is chemically and physically uniform or homogeneous throughout.

In one embodiment, the multiparticulates contain a solid dispersion of drug in one or more excipients. In some embodiments, the one or more excipients have a low peroxide content in order to reduce oxidation of the drug or excipients.

The solid dispersion can be created by homogeneously dispersing the drug, in the form of fine particles, within the one or more excipients. More preferably, the solid dispersion is formed by partially dissolving the drug in molten excipient(s) or partially dissolving the drug with the excipient(s) in a mutual solvent (e.g., methylene chloride) during the formulation of the multiparticulates. In another embodiment, the multiparticulates contain a solid solution of drug and one or more excipients. In some embodiments, to create a solid solution, the drug is completely solubilized in the molten excipient(s) or completely dissolved with the excipient(s) in a co-solvent (e.g., methylene chloride) during the formulation of the multiparticulates. This is accomplished through the selection of materials and the manner in which they are processed.

Preferred excipients appropriate for the preparation of drug containing multiparticulates, or that are found in the final formulation, either dissolve slowly in water or are insoluble in water. As used herein, the term "dissolves slowly in water" refers to materials that are not completely dissolved in water within a period of 30 minutes. Suitable materials include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited, to the conjugate bases of the fatty acid (i.e., the carboxylate ion), fatty acid esters, fatty acid glycerides (mono-, di- and tri-glycerides), fatty amines, and hydrogenated fats. Specific examples include, but are not limited to stearic acid, palmitic acid, myristic acid, lauric acid, capric acid, hydrogenated vegetable oil, hydrogenated cottonseed oil, hydrogenated castor oil, hydrogenated oils available under the trade name Sterotex®, cocoa butter, glyceryl behenate (available under the trade name COMPRITOL 888®), glyceryl dipalmitostearate (available under the trade name PRECIROL®), and stearyl alcohol. Suitable waxes and wax-like materials include natural or synthetic waxes, hydrocarbons, and normal waxes. Specific examples of waxes include beeswax, glycowax, castor wax, carnauba wax, paraffins, microcrystalline wax and candelilla wax. As used herein, a wax-like material is defined as any material which is normally solid at room temperature and has a melting point of from about 30 to 300° C. Certain polymers may also be used as excipients in the formulation of drug containing multiparticulates. Suitable polymers include ethylcellulose and other natural or synthetic cellulose derivatives. Polymers which are slowly soluble and form a gel in an aqueous environment, such as hydroxypropyl methylcellulose or polyethylene oxide (e.g., PEO-PPO block copolymers) may also be suitable as excipients for drug containing multiparticulates.

In some cases, it may be desirable to incorporate one or more substances into the formulations, contemplated herein to change the dissolution behavior or the physical and/or chemical stability of the formulation. In some embodiments, these substances alter the rate of water penetration into the hydrophobic drug containing multiparticulates, thereby changing the dissolution behavior of the formulation. Non-limiting examples of such substances include rate-controlling (wicking) agents. Such agents may be formulated along with the fats or waxes listed above. Examples of rate-controlling materials include certain starch derivatives (e.g., waxy maltodextrin and drum dried corn starch), cellulose derivatives (e.g., hydroxypropylmethylcellulose, hydroxypropylcellulose, methylcellulose, and carboxymethylcellulose), polyvinyl pyrrolidone, alginic acid, and lactose or mixtures thereof.

Additionally, a pharmaceutically acceptable surfactant, for example, lecithin, sodium dodecyl sulfate, poloxamer, Cremophor (polyethoxylated castor oil), Polyoxylglycerides (e.g., polyethylene glycol fatty acid esters), sorbitan stearates, or polysorbates, or mixtures of two or more surfactants, may be added to alter the dissolution behavior of the multiparticulates. Other acceptable surfactants include inorganic salts of fatty acids (e.g., potassium and sodium salts of fatty acids). Mixtures of mono-, di- and tri-glycerides and mono- and di-fatty acid esters of polyethylene glycol, available under the trade name such as GELUCIRE® or Myrj® are also suitable. In some embodiments, the surfactants are present in the multiparticulates, are applied to the surface to the multiparticulates, are blended with the multiparticulates or a combination thereof. Other inactive ingredients, such as hydroxypropylmethylcellulose, poloxamer or polyvinyl pyrrolidone may also be added as needed to impart a desirable attribute such as inhibiting crystallization of one or more components of the multiparticulates.

In some cases, suitable antioxidants may be added to the composition. Anti-oxidants include, but are not limited to, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA). Chelating agents may also be needed. Suitable chelating agents include, but are not limited to, EDTA, a salt of EDTA, desferrioxamine B, deferoxamine, dithiocarb sodium, penicillamine, pentetate calcium, a sodium salt of pentetic acid, succimer, trientine, nitrilotriacetic acid, trans-diaminocyclohexanetetraacetic acid (DCTA), diethylenetriamine-pentaacetic acid, bis(aminoethyl)glycolether-N,N,N',N'-tetraacetic acid, iminodiacetic acid, citric acid, tartaric acid, fumaric acid, or a salt thereof.

Encapsulation or incorporation of drug into excipient(s) to produce drug containing multiparticulates can be achieved through known pharmaceutical formulation techniques. To create a composition that protects drug from exposure upon mechanical disruption (e.g., grinding, chewing, or chopping), the drug is intimately dispersed within the one or more excipients. In the case of formulation in fats, waxes or wax-like materials, the one or more excipients are heated above their melting temperature and the drug is added to form a mixture where drug particles are suspended in the one or more excipients, where the drug is dissolved in the one or more excipients, or a mixture where a portion of the drug particles are suspended in the one or more excipients and another portion of the drug is dissolved in the one or more excipients. Multiparticulates can be subsequently formulated through several methods including, but not limited to, spray congealing, spray chilling, spray drying, extrusion, bulk congealing into capsules and bulk congealing with subsequent milling. In a preferred process, one or more excipients are heated above its melting temperature, the drug is added, and the molten excipient-drug mixture is congealed to form solid, spherical particles via a spraying process using one or more nozzles, a spinning cylinder or a spinning disc. Alternatively, the molten excipient-drug mixture can be found in "Remington—The science and practice of pharmacy", 20th edition, Jennaro et. al., (Phila, Lippencott, Williams, and Wilkens, 2000.

In a preferred process, spherical or substantially spherical particles are produced. Spherical particles may introduce an additional barrier to deter tampering with the composition. Smaller, round or substantially round particles act as "ball bearings" that are more difficult to crush or grind, and if crushed, do not allow for significant enough decrease in particle size or surface areas of the particles in order to have a significant and adverse effect on release rate.

In a preferred embodiment, multiparticulates include a solid solution of drug and one or more excipients. One approach to achieving a solid solution is to formulate a salt composed of a pharmaceutically active agent and one or more fatty acids or amine along with other waxy and/or fatty excipients. In this embodiment, the salt may be formed during the formulation process itself. To accomplish this, the one or more fatty acids or amines are melted and mixed with the free base or acid form of the active agent at a temperature above the melting point(s) of the fatty acid(s) or amine(s). One or more additional excipients including but not limited to fat, fatty substance(s), wax, wax-like substance(s), polymeric substances, or antioxidants can be included in the molten mixture. The molten solution is then formulated into multiparticulates via, e.g., spray congealing, spray chilling, spray drying, extrusion, bulk congealing into capsules and bulk congealing with subsequent milling.

In some embodiments, the molar concentration of fatty acid or amine may need to be higher than that of the drug in order to achieve a homogeneous single phase during the melt process. For example, it has been found that, for oxycodone, a molar ratio in excess of about 7:1 fatty acid (e.g., myristic acid) to drug results in a homogeneous melt using this technique. The molar ratio needed to obtain a homogeneous melt may depend on the type and quantity of additional excipients added. For example, some fat or wax excipients, such as natural waxes (e.g. beeswax and carnauba wax) may contain free fatty acids or other components that can interact ionically with the drug. Such fat or wax excipients may reduce the amount of fatty acid excipient required to obtain a homogeneous melt as compared to fat or wax excipients that do not interact with the drug. In one embodiment, the molar ratio of fatty acid or fatty amine to drug is from about 1:1 to about 15:1, preferably from about 6:1 to about 15:1. However, molar ratios greater than 15:1, for example 15:1 to 25:1, preferably 15:1-20:1, may be required depending on the fatty acid or fatty amine, the drug to be formulated, and/or the additional excipient(s).

For some excipients it may be desirable to use a solvent evaporation technique to produce drug containing multiparticulates. In this case drug and one or more excipients are co-dissolved in a mutual solvent and excipients can subsequently be produced by several techniques including, but not limited to, forming an emulsion in water or other appropriate media, spray drying or by evaporating the solvent from the bulk solution and milling the resulting material.

In addition to modification of the drug itself, processing conditions can be used to influence the dispersion of the drug within water-insoluble or slowly water soluble materials. For example, in the case where the water insoluble or slowly soluble material is melted and the drug is fully or partially dissolved under stirring conditions, the temperature, agitation rate and time of processing will influence the degree of dissolution achieved. More specifically, a more homogeneous dispersion may be achieved with a higher temperature, faster stirring rate and/or longer processing time. Ultrasound can also be applied to the molten mixture to increase the degree of dispersion and/or the rate of dissolution of the drug.

In some embodiments, the drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

D. Coated Drug Containing Multiparticulates

In some embodiments, drug containing multiparticulates or drug particles are encapsulated. Drug containing multiparticulates can be encapsulated in water insoluble materials, slowly water soluble materials, organic insoluble materials and/or materials with pH dependent solubilities.

In general, any coating procedure which provides a contiguous coating on each multiparticulate can be used. Coating procedures known in the arts include, but are not limited to, fluid bed coating processes and microencapsulation. Detailed descriptions of these processes can be found in "Remington—The science and practice of pharmacy", 20th Edition, Jennaro et al., (Phila, Lippencott, Williams, and Wilkens, 2000.

The water-insoluble coating materials may be selected from natural or synthetic film-formers used along, in admixture with each other, or in admixture with plasticizers, pigments and other substances to alter the characteristics of the coating. A water-insoluble but water-permeable diffusion barrier may contain ethyl cellulose, methyl cellulose and mixtures thereof. The water-permeable diffusion barrier may also include ammonio methacrylate copolymers sold under the trade name EUDRAGIT® (Rohm Pharma), such as EUDRAGIT RS, EUDRAGIT RL, EUDRAGIT NE and mixtures thereof. Other synthetic polymers, for example, polyvinyl acetate (available under the trade name KOLLICOAT®), can also be used to form water-insoluble but permeable coatings.

The coating may also include a water-insoluble but enzymatically degradable material. In some instances the substrates of digestive enzyme are naturally water-insoluble and can be utilized in the formulation without further processing. Solid esters of fatty acids, which are hydrolyzed by lipases, can be spray coated onto multiparticulates or drug particles. Mixtures of waxes (beeswax, carnauba wax, etc.) with glyceryl monostearate, stearic acid, palmitic acid, glyceryl monopalmitate and cetyl alcohol will also form films that are dissolved slowly or broken down in the GI tract. Zein is an example of a naturally water-insoluble protein. It can be coated onto drug containing multiparticulates or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. In some embodiments, chemical cross-linking agents are used. Examples of chemical cross-linking agents include, but are not limited to, aldehydes (e.g., gluteraldehyde and formaldehyde), epoxy compounds, carbodiimides, and genipin. In addition to these cross-linking agents, oxidized and native sugars have been used to cross-ink gelatin. Cross-linking can also be accomplished using enzymatic means; for example, transglutaminase has been approved as a GRAS substance for cross-linking seafood products. Finally, cross-linking can be initiated by physical means, for example application of a stimulus, such as heat, UV irradiation, and gamma irradiation.

To produce a coating layer of cross-linked protein surrounding drug containing multiparticulates or drug particles, a water soluble protein can be spray coated onto the multiparticulates and subsequently cross-linked by one of the methods described above. Alternatively, drug containing multiparticulates can be microenapsulated within protein by coacervation-phase separation, for example, by the addition of salts and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions. Insoluble coatings can be formed on particles in this fashion. It should be noted that in many cases polysaccharides are broken down specifically by enzymes produced by bacteria within the colon.

In some cases a water-insoluble but enzymatically degradable coating including both a protein and a polysaccharide can be produced if the components are oppositely charged polyelectrolytes. Under the proper temperature, pH, and concentrations, the two polymers can interact through their opposite electrical charge and form a water-insoluble complex. If a core particle is present at the time the complex phase separates, it will be coated. For example, gelatin and gum arabic can be coated onto a core particle utilizing this process. Optionally, the complex can be made irreversibly insoluble by subsequent cross-linking induced by chemical or physical means.

Coating materials may also include a pH sensitive polymer which is insoluble in the acid environment of the stomach, and soluble in the more basic environment of the GI tract. These coatings, referred to as enteric coatings, create a dosage form designed to prevent drug release in the stomach. Preventing drug release in the stomach has the advantage of reducing side effects associated with irritation of the gastric mucosa and/or of minimizing exposure of drug to very low pH. Avoiding release within the stomach can be achieved using enteric coatings known in the art. The enteric coated formulation remains intact or substantially intact in the stomach, however, once the formulation reaches the small intestines, the enteric coating dissolves and exposes either drug-containing carrier particles or drug-containing carrier particles coated with extended release coating.

Enteric coated particles can be prepared as described in "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et. al., (Media, Pa.; Williams and Wilkins, 1995). Examples of suitable coating materials include, but are not limited to, cellulose polymers, such as cellulose acetate phthalate, hydroxypropyl cellulose, hydroxypropyl methylcellulose phthalate and hydroxypropyl methylcellulose acetate succinate; polyvinyl acetate phthalate, acrylic acid polymers and copolymers, and certain methacrylic resins that are commercially available under the trade name EUDRAGIT® (Rohm Pharma). Additionally the coating material may contain conventional carriers such as plasticizers, pigments, colorants, glidants, stabilization agents, and surfactants.

In some cases it may be desirable to coat the particles with a coating which is soluble in aqueous solutions but insoluble in hydroalcoholic solutions. In this case the coating material may or may not have pH sensitive solubility in aqueous solutions.

In other cases it may be desirable to combine coating materials to produce a tailored release of drug. For example, combinations of insoluble polymers and pH dependent polymers can produce a pH dependent sustained release profile. Combinations of insoluble polymers (e.g., ethylcellulose), water-soluble polymers (e.g., HPMC or PEG) and pH dependent sustained release profiles.

In one embodiment, the particles are coated with cellulose acetate phthalate. Cellulose acetate phthalate is typically used as an enteric coating.

E. Control of Oxidative Degradation

In some cases it may be necessary to prevent oxidative degradation of the active pharmaceutical ingredient and/or the one or more inactive excipients in the composition. Oxidation of one or more components may occur during the formulation process itself or during the shelf-life of the composition. Oxidation may result from exposure to the oxygen content of air or, alternatively, may be related to impurities in the excipients. For example, highly reactive species such as peroxides, hydro-peroxides superoxides, hypochlorites and/or formic acid may be present in excipients as manufacturing or raw-material-related impurities. Also, trace metal impurities in excipients, such as iron and copper, can catalyze oxidation reactions. Several approaches may be taken to reduce or eliminate reactions involving oxygen in the composition. In one embodiment, an antioxidant may be included on the composition to mitigate the degradation of the drug in such cases. If the source of oxidation is a reactive manufacturing-related impurity in one or more of the excipients, the anti-oxidant can be co-melted with the excipient(s) in order to protect the drug from these reactive species.

Chelating agents may also be employed to scavenge trace metals. Controls over the exposure to environmental oxygen may also be employed. For example, in embodiments where a melt process is employed, a closed tank can be used. An inert gas, such as nitrogen or argon, can be sparged through the melt and/or introduced into the head space of the tank. The inert can also be introduced following vacuum removal of environmental oxygen.

Suitable antioxidants include, but are not limited to, butylated hydroxytoluene (BHT); ascorbic acid, its salts and esters; Vitamin E, tocopherol and its salts; sulfites such as sodium metabisulphite; cysteine and its derivatives; citric acid; propyl gallate; and butylated hydroxyanisole (BHA). Suitable chelating agents include, but are not limited to, EDTA, a salt of EDTA, desferrioxamine B, deferoxamine, dithiocarb sodium, penicillamine, pentetate calcium, a sodium salt of pentetic acid, succimer, trientine, nitrilotriacetic acid, trans-diaminocyclohexanetetraacetic acid (DCTA), diethylenetriamine-pentaacetic acid, bis(aminoethyl)glycolether-N,N,N',N'-tetraacetic acid, iminodiacetic acid, citric acid, tartaric acid, fumaric acid, or a salt thereof.

The concentration of the antioxidant is generally from about 0.001% to about 1% w/w, preferably from about 0.01% to about 0.5% w/w. However, concentrations of less than 0.001% or greater than 0.5% may be used, provided the concentration is sufficient to stabilize the formulation and is non-toxic.

In some instances it may be advantageous to reduce or eliminate the presence of reactive species within the excipients. This is particularly true for multiparticulates in which a hot melt process is used to create a solid dispersion or solid solution. It has been demonstrated that controlling the peroxide value in carnauba wax, for example, can reduce the formation of oxidation by-products. Depending on the specific ratio used in the formulation, waxy materials, such as carnauba wax, with a peroxide value less than 25 ppm, more preferably less than 5 ppm, and most preferably less than 3 ppm are preferred in some embodiments.

F. Dosage Forms

In one embodiment a drug is partially dissolved within a water-insoluble or slowly water soluble material during the manufacturing process, for example, by mixing at a temperature above the melting point of the excipients, and the mixture is formulated into multiparticulates. In a preferred embodiment a drug is fully dissolved within a water-insoluble or slowly water soluble material during the manufacturing process, for example, by mixing at a temperature above the melting point of the excipients, and the mixture is formulated into multiparticulates. In still a further embodiment, the drug containing multiparticulates, where the drug is homogeneously dispersed in a particulate form, or has been partially or fully dissolved within one or more excipients during the manufacturing process, are coated with one or more coatings to form coated multiparticulates.

The multiparticulates, coated multiparticulates, or a mixture thereof are formed into a solid dosage form suitable for oral administration. For example, multiparticulates or coated multiparticulates can be incorporated into hard shell capsules, dispersed within a soft gelatin capsule, or tableted by compression. Appropriate excipients, such as magnesium stearate as a lubricant, colloidal silicon dioxide as a glidant, sodium starch glycolide, sodium croscarmellose or crospovidone as a disintegrant, and lactose or microcrystalline cellulose as fillers may be included.

Examples of suitable hard shell capsules include capsules formed from gelatin, hydroxypropylmethylcellulose, polysaccharide, and other pharmaceutically acceptable polymer materials. In some embodiments hydroxypropylmethylcellulose capsules, marketed under the trade name Vcaps®, can be employed.

In some embodiments, drug containing multiparticulates are blended with extragranular material and filled into hard shell capsules. The extragranular material can serve several functions. One or more extragranular materials, such as lubricants or glidants, can be used to keep the multiparticulates from sticking together. Examples of suitable materials for this purpose include, but are not limited to, magnesium stearate, zinc stearate, colloidal silicone dioxide, talc, starch, calcium stearate, hydrogenated vegetable oils, stearic acid, sodium stearyl fumarate, sodium benzoate, sodium acetate, leucine, sodium oleate, sodium lauryl sulfate, magnesium lauryl sulfate and polyethylene glycol. In other embodiments, the extragranular material is a natural or synthetic gel forming excipient, added to form a gel or viscous environment around the particles when exposed to an aqueous environment. Extragranular material of this type can be used to modulate the release of drug from the dosage form. Examples of suitable materials include, but are not limited to, hydroxypropylmethylcellulose, sodium carboxymethylcellulose, polyvinyl pyrrolidone and sodium alginate.

In some embodiments, the compositions are coated with an enteric coating. Enteric coatings known in the art are applied directly to the abuse-deterrent multiparticulate or coated multiparticulate compositions or are applied to the surface of a capsule or tablet containing the abuse deterrent multiparticulate and/or coated multiparticulate compositions. Enteric coatings known in the art include, for example, acrylic polymers that are commercially available under the trade name EUDRAGIT®, cellulose acetate phthalate, hydroxypropylmethyl-cellulose phthalate, polyvinylacetate phthalate, shellac, hydroxypropyl-methylcellulose succinate, cellulose acetate trimelliate or mixtures thereof. In one embodiment, the particles are coated with cellulose acetate phthalate.

Dosage forms can include one or more drugs. When the dosage form includes two or more drugs they can be Scheduled drugs or can be a combination of Scheduled and non-Scheduled drug. The drugs can be incorporated into the same multiparticulates. Alternatively, the drugs can be incorporated into separate multiparticulate compositions where the Scheduled drugs are incorporated into abuse deterrent multiparticulate compositions and the non-Scheduled drugs are incorporated into abuse deterrent multiparticulate compositions, sustained release compositions known in the art or immediate release compositions known in the art. The compositions containing the different drugs can be formulated into a single solid dosage form suitable for oral administration; for example, they can be incorporated into a hard capsule shell, or combined with appropriate excipients and compressed into a tablet form.

Examples of non-scheduled drugs that may be included in dosage forms described herein include, but are not limited to, aspirin, acetaminophen, non-steroidal anti-inflammatory drugs, cyclooxygenase II inhibitors, N-methyl-D-aspartate receptor antagonists, glycine receptor antagonists, triptans, dextromethorphan, promethazine, flocinal, guaifenesin, butalbital, and caffeine.

An immediate release dose can be incorporated into the formulation in several ways. Immediate release multiparticulates can be made utilizing standard methodologies and formulated along with abuse-deterrent multiparticulate and/or coated multiparticulate compositions in a suitable oral dosage form. Alternatively, a coating containing drug which is available for immediate release can be placed on a tablet containing abuse-deterrent multiparticulate and/or coated multiparticulate compositions plus appropriate excipients. Additionally, an immediate dose of drug can be granulated or blended with rapidly dissolving excipients and subsequently compressed (1) as one layer of bi-layer tablets in which the abuse-deterrent multiparticulate and/or coated multiparticulate compositions are compressed as the other layer, or (2) as the outer layer of compression-coated tablets in which the abuse-deterrent multiparticulate and/or coated multiparticulate compositions are compressed as the inner core, or (3) into tablets in which abuse-deterrent multiparticulate and/or coated multiparticulate compositions are embedded.

In some embodiments, the immediate release portion of the dosage form contains a lipophilic drug derivative. For example, salt derivatives or complexes that are insoluble at a neutral pH but dissociate, thereby releasing the parent compound, at an acidic pH are ideal for immediate release within the stomach. Exemplary salts, such as salts of oxycodone, that may exhibit this property include, but are not limited to, the tannate, phthalate, salicylate, gallate, pectinate, phytate, saccharinate, asesulfamate and terephthalate salts. Use of salts or complexes in the immediate release portion of the dosage form reduces the abuse potential of the immediate release dose if the formulation is crushed and (1) snorted or (2) dissolved in water since these salts will be poorly soluble under these conditions. It is understood by the one of ordinary skill in the art that such salts or complexes may also be used to formulate an immediate release dosage form without a sustained release portion.

Additional mechanisms to reduce the potential for abuse can also be incorporated during the process of formulating tablets or capsules. For example, ingredients can be added to deter chewing or snorting of the final formulations. For example, an intensely bitter substance may deter chewing, while an intensely spicy ingredient, such as capsaicin, may deter snorting. The addition of a colored dye, which would stain the skin and raucosal surface of the nose following snorting may also serve to reduce this practice.

In some embodiments, the contemplated compositions comprising a plurality of multiparticulates comprise one or more additional excipients that are combined with the multiparticulates. The one or more additional excipients comprise diluents, lubricants, gel forming excipients, and combinations thereof. In other embodiments, each multiparticulate or coated multiparticulate comprises optional excipients including, but are not limited to diluents, binders, lubricants, disintigrants, colorants, plasticizers and the like. Diluents, also termed "fillers," are typically necessary to increase the bulk of a solid dosage form so that a practical size is provided for compression of tablets. Examples of diluents include cellulose, dry starch, microcrystalline cellulose, dicalcium phosphate, calcium sulfate, sodium chloride confectioner's sugar, compressible sugar, dextrates, dextrin, dextrose, sucrose, mannitol, powdered cellulose, sorbitol, and lactose.

Binders are used to impart cohesive qualities powdered materials and can include materials such as starch, gelatin, sugars, natural and synthetic gums, polyethylene glycol, ethylcellulose, methylcellulose, hyroxypropylmethyl-cellulose, carboxymethylcellulose, waxes and polyvinyl pyrrolidone.

Lubricants are used to facilitate tablet and capsule manufacture. Examples of lubricants include talc, magnesium stearate, zinc starate, calcium stearate, hydrogenated vegetable oils stearic acid, sodium stearyl fumarate, sodium benzoate, sodium acetate, leucine, sodium oleate, sodium lauryl sulfate, magnesium lauryl sulfate and polyethylene glycol.

Disintegrants can be added to pharmaceutical formulations in order to facilitate "breakup" or disintegration after administration. Materials used for this purpose include starches, clays, celluloses, aligns, gums, and cross-linked polymers.

A plasticizer may be included in coating materials to alter their mechanical properties. Examples of plasticizers include benzyl benzoate, chlorobutanol, dibutyl sebacate, diethyl phthalate, glycerin, mineral oil, polyethylene glycol, sorbitol, triacetin, triethyl citrate, glycerol, etc.

One or more surfactants may also be added to the final dosage form to modulate the release of drug from the multiparticulate composition. Examples include, but are not limited to, lecithin, sodium dodecyl sulfate, poloxamer, Cremophor, polysorbates, and polyoxyglycerides.

In addition to the additives above, coloring and flavoring agents may also be incorporated into the composition.

II. Methods of Making

The compositions described herein can be made using a variety of techniques known in the art including, but not limited to, spray congealing, spray chilling, spray drying, extrusion, bulk congealing into capsules and bulk congealing with subsequent milling. In one embodiment, beads containing the active agent or a fatty acid salt thereof and recipients are prepared via spray congealing utilizing a spinning disc atomization process. In this process, a molten mixture or solution of the active agent and excipients is pumped onto a heated, rotating disc. The disc generates centrifugal force which distributes the melt as a uniform sheet and accelerates it toward the edge of the disc where it forms ligaments that break into droplets that rapidly congeal into beads having diameters in microns. The disc can alternatively incorporate vanes that channel the melt at the periphery of the disc. A general description of apparatuses that employ such a rotating disc may be found, e.g., in U.S. Pat. Nos. 7,261,529 and 3,015,128, both of which are incorporated by reference as if fully set forth herein.

Process parameters such as disc speed, melt feed rate, melt feed temperature, and/or air flow can affect bead size and/or bead size distribution. Under some circumstances, feed rate has little effect on the median bead size or distribution (span). In some instances, bead size can be decreased with increased disc speed and low air flow rates. In still other instances, the span can be decreased with increased disc speed and high feed temperatures.

In some embodiments, the temperature at which the melt is manufactured is controlled in order to avoid significant degradation of drug and/or carrier material. In some embodiments, the melt preparation and processing temperature is higher than the melting point of the bead formulation, i.e. the temperature at which the melt is completely liquid, by 1-30° C., preferably 1-5° C. higher, to minimize potential product degradation and/or adverse side reactions.

Melt feed temperature, the temperature at which the melt is fed onto, e.g., a spray congealing device, should also be 1-30° C. higher than the melting point, preferably be 3-10° C. higher than the melting point to minimize the amount of heat that needs to dissipate from the beads before they congeal.

In one embodiment, the multiparticulates have a D(0.1) particle size from about 50 to about 250 μm, preferably from about 140 to about 190 μm; a D(0.5) median particle size from about 150 to about 750 μm, preferably from about 200 to about 400 to about 700 μm. The multiparticulates are characterized by span (i.e., [D(0.9)-D(0.1)]/D(0.5)) less than 5, preferably less than 2, and more preferably less than 1.4. In some embodiments, multiparticulates having a span of less than 1.4 are less prone to segregation during processing and/or are more likely to achieve the desired pharmacokinetic profile. D(0.1), D(0.5) and D(0.9) are defined as the diameters where 10%, 50% or 90% w/w of the microparticles have a smaller diameter, respectively, when measured, e.g., using a laser diffraction technique. The terms "D(0.5)" and "median particle size" are used interchangeably herein. The multiparticulates can be any geometrical shape. In some embodiments, the multiparticulates may be irregular, oblong or spherical in shape. In a preferred embodiment, the multiparticulates are substantially round or spherical in shape (e.g., beads).

Disc speed, feed rate and air flow rate depend on the melt formulation and desired size and span. Bead with spans less than 5 may be produced. Conditions that yield a narrow span are preferred to avoid significant particle segregation during downstream processing. A span of less than about 2, and more preferably less than about 1.4 is preferred.

II. Methods of Administration

In addition to providing a deterrent to common methods of abuse/diversion, the formulation can provide a sustained release of drug over an extended time period. This is a natural consequence of the fact that, in the formulations described herein, drug is slowly released from a predominantly water-insoluble, hydrophobic matrix as it passes through the GI tract. The barrier components may be degraded as the matrix passes through the GI tract, for example, by enzymes, the surfactant action of bile acids, and/or mechanical erosion.

In some embodiments, an immediate release of drug is achieved within the stomach in order to provide rapid therapeutic onset.

The pharmaceutical drug composition is generally administered orally. The appropriate dosage formulations can be obtained by calculation of the pharmacokinetics of the formulation, then adjusting using routine techniques to yield the appropriate drug levels based on the approved dosage forms. Any suitable amount of drug containing multiparticulates or coated multiparticulates can be included in the final formulation. The selection of a suitable amount of drug containing multiparticulates depends on the dosage desired and is readily determined by those skilled in the art.

In addition to oral administration, some embodiments may also be determined by other routes, including, but not limited to, rectal and nasal administration. Some embodiments may also be suitable for formulation as oral liquids.

The present composition and method of making and using the composition will be further understood by reference to the following non-limiting examples.

Example 1: Preparation of Drug Containing Multiparticulates

TABLE 1

Compositions

| Ingredient | Composition of Formulation A | Composition of Formulation B | Composition of Formulation C | Composition of Formulation D |
|---|---|---|---|---|
| Oxycodone Base | 5 g | 5 g | 10 g | 5 g |
| Myristic Acid | — | — | 50 g | 30 g |
| Stearic Acid | 34 g | 34 g | — | — |
| Yellow Beeswax | 10 g | — | 10 g | 10 g |
| Carnauba wax | 5 g | 10 g | 20 g | 10 g |

Procedure:
1. Fatty acid (myristic or stearic acid) was melted in an erlenmeyer flask in a silicone oil bath at 100° C. the mixture was stirred and kept under an argon blanket for this and all subsequent steps.
2. Oxycodone base was introduced into the molten fatty acid and the melt was stirred until the oxycodone base was completely dissolved and a clear liquid was formed.
3. Yellow beeswax was added and dissolved under constant stirring.
4. Carnauba wax was added and dissolved under constant stirring.
5. The resulting homogeneous molten solution was poured onto aluminum foil and allowed to solidify at room temperature.
6. The bulk material obtained was combined with small quantities of dry ice and subjected to size reduction in a mortar and pestle.
7. The dry ice was allowed to dissipate and the particles were sieved to obtain various size ranges. Particles 20-40 mesh in size (400-841 micron) were subjected to testing.

Example 2: Release of Drug from Crushed Multiparticulates

In vitro testing was conducted in order to assess the influence of crushing of the multiparticulates produced in Example 1 on the release in simulated stomach conditions. A currently marketed sustained release formulation of oxycodone, OxyContin®, was also subjected so crushing and dissolution for comparison purposes.

Multiparticulates (Formulations A, B, C or D, all 20-40 mesh in starting particle size) and OxyContin® tablets were crushed using a glass mortar and pestle. The resulting crushed material was placed in a dissolution vessel equipped with paddles (USP Apparatus II). 900 mL of 0.1N HCl pre-warmed to 37° C. was added to the vessels and stirred for 15 minutes. After 15 minutes the amount of oxycodone released was determined. The results are shown in Table 2.

TABLE 2

Drug Release from Crushed Compositions

| Sample | % Released in 15 minutes in 0.1N HCl (n = 3) |
|---|---|
| Oxycontin ® (40 mg Tablet) | 95.6 +/− 2.7 |
| Formulation A (multiparticulates containing 40 mg oxycodone HCl equivalent) | 31.6 +/− 2.6 |
| Formulation B (multiparticulates containing 40 mg oxycodone HCl equivalent) | 19.7 +/− 1.4 |
| Formulation C (multiparticulates containing 20 mg oxycodone HCl equivalent) | 14.8 +/− 1.1 |
| Formulation D (multiparticulates containing 20 mg oxycodone HCl equivalent) | 18.2 +/− 1.6 |

As illustrated in the table above, the multiparticulate compositions of Example 1 release only a fraction of the total drug load in simulated stomach conditions when crushed. In contrast, a currently marketed sustained release composition, OxyContin®, releases approximately 96% of the drug load when crushed and exposed to identical conditions.

Example 3: Preparation of Oxycodone Containing Multiparticulates Using a Spinning Disc Atomization Process Batch size: 1000 g

TABLE 3

| Composition | |
|---|---|
| Component | Quantity (g)/Batch |
| Oxycodone base | 91 |
| Myristic acid | 545 |
| Beeswax | 182 |
| Carnauba Wax | 182 |
| Total | 1000.0 |

Procedure:
1. Myristic acid was melted at 85° C. in a silicone oil bath while constantly flowing argon above the surface of the solution.
2. Beeswax was added to the molten fatty acid and mixed until a clear, homogeneous solution was obtained.
3. Carnauba wax was added to the molten solution and mixed until a clear, homogeneous solution was obtained.
4. Oxycodone base was added to the molten solution and mixed until a clear, homogeneous solution was obtained.

The resulting molten solution was transferred to a feed kettle and continuously metered onto a spinning disc atomizer (see FIG. 1) in order to form solid, spherical multiparticulates. These multiparticulates can be optionally spay coated with, for example, cellulose acetate phthalate.

Example 4: Preparation of Coated Drug Containing Multiparticulates

The drug-containing particulates from Example 3 can be spray coated with cellulose acetate phthalate.

Example 5: Preparation of Oxymorphone Containing Multiparticulates

Batch size: 630.6 g

TABLE 4

| Composition | |
|---|---|
| Component | Quantity (g)/Batch |
| Oxymorphone base | 60 |
| Stearic Acid | 420 |
| Beeswax | 30 |
| Carnauba Wax NF | 120 |
| Butylated Hydroxyanisole | 0.6 |
| Total | 630.6 |

Procedure:
1. Stearic acid was melted in an erlenmeyer flask in a silicone oil bath at 100° C. Note the composition was subjected to stirring and was kept under an argon blanket for this and all subsequent steps.
2. Butylated hydroxyabisole was added to the molten stearic acid while mixing.
3. Oxymorphone base was introduced into the molten fatty acid and the melt was stirred until all oxymorphone base dissolved and a clear liquid was formed.
4. Beeswax was added and dissolved under constant stirring.
5. Carnauba wax was added and dissolved under constant stirring.
6. The resulting homogeneous molten solution was poured onto aluminum foil and allowed to solidify at room temperature.
7. The bulk wax obtained was combined with dry ice and subjected to size reduction in a mortar and pestle.
8. The dry ice was allowed to dissipate and the particles were sieved to obtain particles in the 40-80 mesh size range.

Example 6: Preparation of Capsules for Oral Administration

The drug containing multiparticulates from Examples 1, 3, 4, and 5 can be blended with one or more suitable lubricants and, optionally, one or more glidants, and incorporated into an appropriately sized hard shell capsules.

Example 7: Use of Spray Nozzles to Prepare Oxymorphone Formulation Beads Containing Additives The formulations in Table 5 were prepared using laboratory-scale melt and spray congealing process using a spray nozzle to form beads. Base formulation components [stearic acid (SA), beeswax (BW) and carnauba wax (CW)] were successively added to a stainless steel beaker equipped with a heating water jacket and allowed to melt with stirring at a controlled temperature of approximately 85° C. Additives such as polymers (PVP K29/32, polyvinyl pyrrolidone), surfactants such as Gelucire 50/13 (Gattefosse, mono- and di-$C_{16}$ and $C_{18}$ fatty acid esters of polyethylene glycol, a blend of mono-, di-, and tri-glycerides of $C_{16}$ and $C_{18}$ and some free PEG and fatty acids). Poloxamer 407 (BASF, triblock copolymer consisting of a central hydrophobic block of polypropylene glycol flanked by two hydrophilic blocks of polyethylene glycol), and/or Span 60 (Sorbitan Monostearate) were added in the amount set forth in Table 5, below, and allowed to dissolve in the melt. Oxymorphone free base, the active pharmaceutical ingredient (API), was then added and mixed until complete dissolution occurred, resulting in a clear melt. The formulation was kept blanketed with inert gas throughout the melt manufacture.

Figure 2:
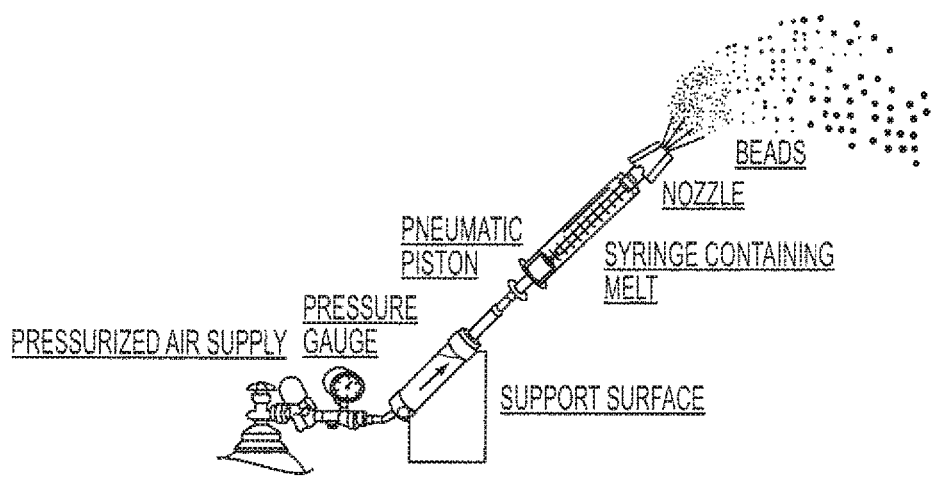
FIG. 2 is a diagram of an exemplary pressure nozzle for the preparation of multiparticulates.

Beads were produced by spraying the melt into an enclosure lined with a plastic sheeting. The melt was sprayed into the enclosure using a syringe equipped with a plastic pressure nozzle at its end. See FIG. 2. The syringe plunger was pressed through the barrel using a pneumatic piston. The piston was activated with an air pressure sufficient to press the melt through the barrel at a speed high enough to atomize the melt and produce beads. Spraying was oriented at approximately 45° angle to provide maximum contact time with room air and thereby allow the beads to cool and congeal before they collect at the bottom of the enclosure. Microscopic examination showed that the resulting product is composed of regular, spherical particles. Particle size can be decreased by increasing air pressure.

TABLE 5

Oxymorphone Formulations prepared using a spray nozzle

| Formulation # | Parts w/w of each Base Formulation component | | | | % of each additive | | | | D(0.5) (μm) |
| --- | --- | --- | --- | --- | --- | --- | --- | --- | --- |
| | API | SA | BW | CW | Poloxamer 407 | Gelucire 50/13 | Span 60 | PVP K29/32 | |
| I | 1 | 8 | 1 | 2 | 0 | 0 | 0 | 0 | 540 |
| II | 1 | 8 | 1 | 2 | 0 | 0 | 0 | 0 | 450 |
| III | 1 | 8 | 3 | 3 | 0 | 0 | 0 | 0 | 435 |
| IV | 1 | 9 | 1 | 2 | 0 | 0 | 0 | 0 | 388 |
| V | 1 | 8 | 1 | 2 | 0 | 0 | 5% | 0 | 416 |
| VI | 1 | 9 | 1 | 2 | 0 | 0 | 0 | 5% | 511 |
| VIII | 1 | 8 | 1 | 2 | 2.5% | 0 | 0 | 0 | 499 |
| IX | 1 | 8 | 1 | 2 | 0 | 2.5% | 0 | 0 | 381 |
| X | 1 | 8 | 1 | 2 | 0 | 1.5% | 3% | | 366 |

Example 8: Use of Spray Nozzles to Prepare Oxycodone Formulation Beads Containing Additives The same procedure as in Example 6 was used to produce beads of Oxycodone formulation. The basic formulation includes the drug, a fatty acid [lauric acid (LA), myristic acid (MA) or stearic acid (SA)], beeswax (BW), carnauba wax (CW) and/or microcrystalline wax (MW, multi-wax). Table 6 lists the formulations and their median particle size.

TABLE 6

Oxycodone Formulations Prepared using a Spray Nozzle

| Formulation # | Parts w/w of each Base Formulation Component | | | | | | | % of each additive | | | D(0.5) (μm) |
| --- | --- | --- | --- | --- | --- | --- | --- | --- | --- | --- | --- |
| | API | LA | MA | SA | BW | CW | MW | Gelucire 50/13 | LA | PEG 1450 | |
| I | 1 | 0 | 6 | 0 | 0.5 | 3.5 | 0 | 0 | 0 | 0 | 197 |
| II | 1 | 0 | 6 | 0 | 0.5 | 3.5 | 0 | 0 | 0 | 0 | 206 |
| III | 1 | 0 | 0 | 8 | 2 | 2 | 0 | 3 | 0 | 0 | 237 |
| IV | 1 | 0 | 0 | 9 | 0 | 0 | 3 | 3 | 0 | 0 | 250 |
| V | 1 | 0 | 0 | 8 | 1 | 2 | 0 | 2 | 0 | 0 | 447 |
| VI | 1 | 0 | 0 | 8 | 1 | 2 | 0 | 2 | 5 | 0 | 345 |
| VIII | 1 | 0 | 0 | 8 | 1 | 2 | 0 | 1.5 | 0 | 1.5 | 292 |
| IX | 1 | 5 | 0 | 0 | 3 | 3 | 0 | 0 | 0 | 0 | 296 |

Figure 3:
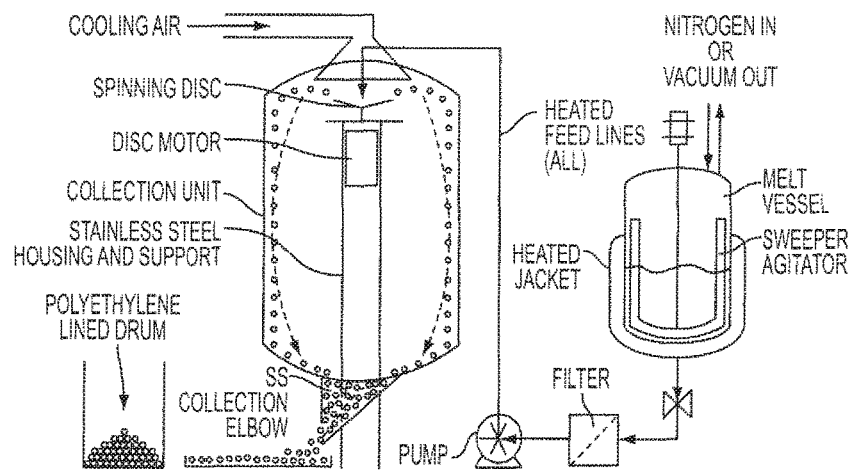
FIG. 3 is a diagram of a large scale apparatus for the production of multiparticulates, where the apparatus comprises a large scale spinning disc atomizer.

Example 9: Use of a Spinning Disc to Prepare Oxycodone Formulations: Effects of Process Parameters on Bead Size, Size Distribution, and Segregation, Batch Size: 160 kg In this example, the melt was manufactured in a jacketed 1300 L stainless steel vessel. Manufacture started by heating the jacket to 85° C. and adding MA to the vessel from the one top of the vessel. The vessel lid was then closed and the MA was melted completely with mixing. The remaining excipients (BW and CW) and the API were vacuum-transferred individually into the melt from the bottom of the vessel. The melt was pumped at a controlled flow rate and temperature onto the center of a 12" diameter spinning disc. The beads were collected at the bottom of a large bead collection chamber. A fan at the top of the chamber was used to pump air with controlled temperature through the collection chamber. See FIG. 3. A 4-factor (feel temperature, disc speed, melt feed rate and fan speed), 2 level, ½ factorial design of experiments (DOE) with 4-center points was conducted to identify critical process parameters and determine their effects on particle size and bead temperature. Eight (8) additional runs were also conducted to extend the range of disc speed and feed rate. Experimental runs were started when process parameters reached their set points. A representative sample from each run was tested for particle size using a Malvern MasterSizer S laser diffraction instrument. Experimental data were analyzed using the Stat-Ease Design Expert Software, Version 7.

Figure 4:
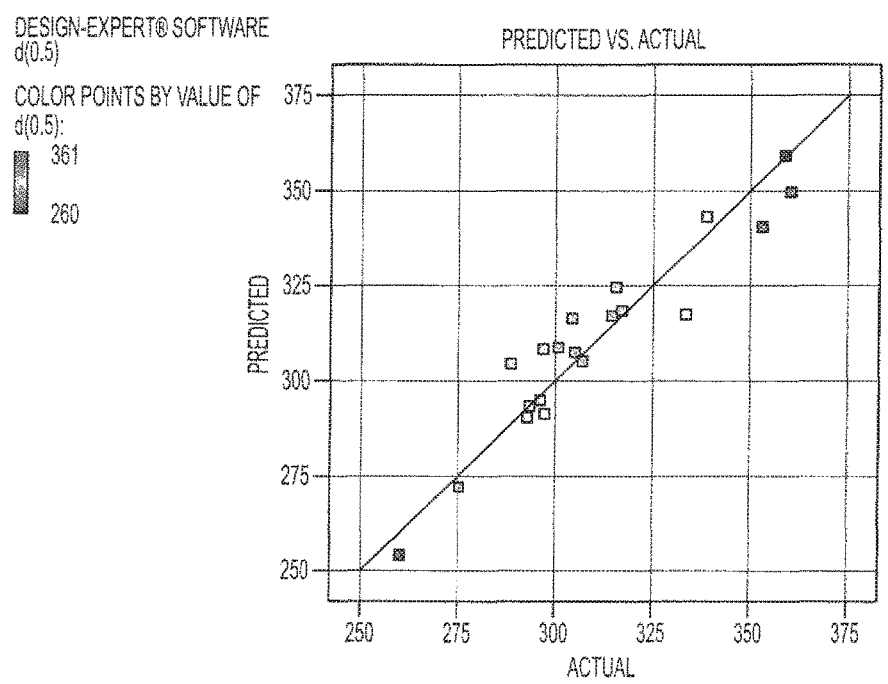
FIG. 4 is a graph showing the D(0.5) median particle size in microns with the actual median particle size in microns.
Figure 5:
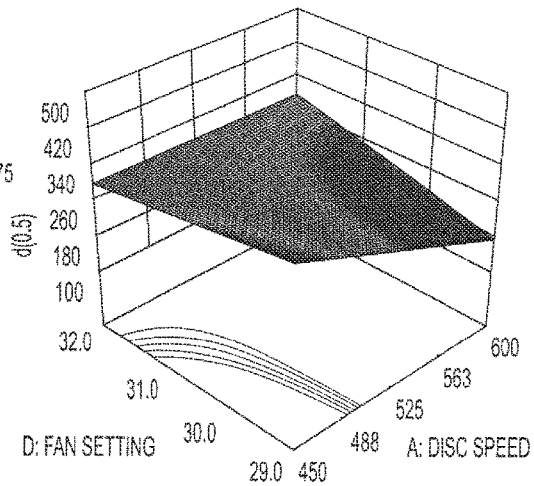
FIG. 5 is a graph showing the D(0.5) median particle size in microns as a function of disc speed (rpm) and fan setting at high feed temperature setting of 90° C., and medium feed rate (pump setting of 3.75 Hz).
Figure 6:
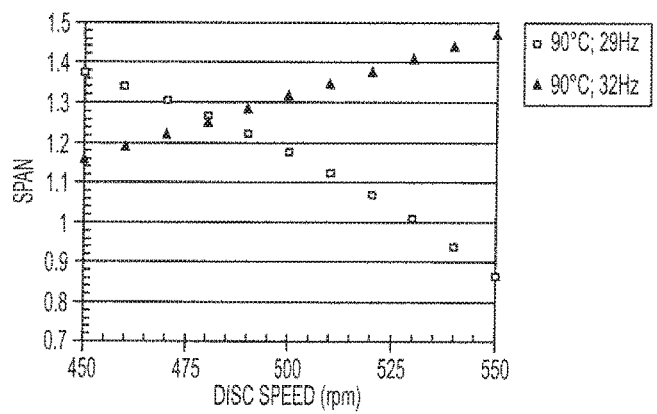
FIG. 6 is a graph showing the effect of disc speed, and air flow rate on the bead size distribution (span) at 90° C.

FIG. 4 shows a good correlation between the predicted median particle size and the actual median particle size for particles made using the process described above. FIG. 5 shows that the size of the beads made by this process decreases with increasing disc speed. FIG. 6 shows that, at low fan speed (29 Hz), the span ([D(0.9)-D(0.1)]/D(0.5)) decreases with increasing disc speed. At high fan speed (32 Hz), the span increases. The large span is an indication of less control over the atomization process at the higher fan speed. High air flow rates associated with high fan speed are thought to interfere with the normal melt spray travel path off the edge of the disc. A similar effect was observed for melts at lower temperature.

A low span (<5) is desirable to minimize segregation of the beads by size during downstream processing such as blending and encapsulation. A span <1.4 is preferred to minimize segregation. A low span may also provide a more desirable pharmacokinetic profile.

Bead segregation during encapsulation can also result in capsules with varying dissolution or release profile. Blending the beads with small levels of additives such as colloidal silicon dioxide serves to reduce the severity of bead segregation.

Example 10: Formulation of Ionic Complex between Oxycodone and Myristic Acid

Samples of oxycodone base; a physical mix (i.e., a non-melted mix) of oxycodone base and a model fatty acid (myristic acid); and a congealed melt of oxycodone base and myristic acid were prepared. The samples were tested by Fourier Transform Infrared (FTIR) spectroscopy, Solid State Carbon-13 ($C^{13}$) nuclear magnetic resonance (NMR), and Solution C-13 and Proton ($H^1$) NMR.

The FTIR study showed the Presence of an IR band at or near 1571 $cm^{-1}$ in the Oxycodone/myristic acid congealed melt not seen in either the free base or Oxycodone/myristic acid physical blend. The band was assigned to a salt of myristic acid and oxycodone formed by interaction of the carboxylic group of myristic acid with the nitrogen in the tertiary amine group of oxycodone. Solid state $C^{13}$ NMR shows significant changes to the oxycodone signals in the congealed melt. For example, significant shifts were observed in the chemical shifts for the bridge carbon atoms adjacent the oxycodone tertiary amine. These results suggest the presence of a long-lived and stable complex or salt of oxycodone and myristic acid.

Although the invention has been described in some detail by way of illustration and example for purposes of clarity of understanding, it will be obvious that certain changes and modifications may be practiced within the scope of the appended claims. Modifications of the above-described modes for carrying out the invention that are within the skill in medicine, pharmacology, microbiology, and/or related fields are intended to be within the scope of the following claims.

All publications (e.g., on-patent literature), patent application publications, and patent applications mentioned in this specification are indicative of the level of skill of those skilled in the art to which this invention pertains. All such publications (e.g., non-patent literature), patent application publications, and patent applications are herein incorporated by reference to the same extent as if each individual publication, patent application publication, or patent application was specifically and individually set forth in its entirety.

We claim:

1. A tamper resistant pharmaceutical composition comprising a plurality of substantially spherical solid particles each particle comprising:
    (a) one or more drugs prone to abuse;
    (b) one or more waxes, wax-like substances or mixtures thereof; and
    (c) one or more fatty acids;
wherein the particles have a median particle size (D[0.5]) between about 200 microns and about 400 microns;
wherein the molar ratio of fatty acid to drug is about 6:1 to about 15:1;
wherein the drug is oxycodone or a pharmaceutically acceptable salt thereof and after oral administration as directed a therapeutically effective amount of drug is released over a period of 6-24 hours; and
wherein the composition maintains a slow release of drug even if the particles are crushed with a mortar and pestle and snorted.

2. The composition of claim 1 wherein the molar ratio of fatty acid to drug is about 7:1 to about 5:1.

3. The composition of claim 1, wherein the drug and the one or more fatty acids interact ionically.

4. The composition of claim 1, wherein the fatty acids are selected from the group consisting of linoleic acid, octanoic acid, capric acid, lauric acid, myristic acid, palmitic acid, stearic acid, oleic acid.

5. The composition of claim 4, wherein the fatty acid is myristic acid.

6. The composition of claim 1, wherein the one or more wax or wax-like substances are selected from the group consisting of beeswax, glycowax, castor wax, carnauba wax, paraffins, microcrystalline wax, and candelilla wax.

7. The composition of claim 6, wherein the wax or wax-like substances are beeswax and carnauba wax.

8. The composition of claim 7, wherein the wax or wax-like substances are beeswax and carnauba wax, and the fatty acid is myristic acid.

9. A method of treating pain comprising administering to a human subject in need thereof, a therapeutically effective amount of a tamper resistant pharmaceutical composition comprising a plurality of substantially spherical particles, each particle comprising:
    (a) one or more drugs prone to abuse;
    (b) one or more waxes, wax-like substances or mixtures thereof; and
    (c) one or more fatty acids;
wherein the particles have a median particle size (D[0.5]) between about 200 microns and about 400 microns;
wherein the molar ratio of fatty acid to drug is about 6:1 to about 15:1;
wherein the drug is oxycodone or a pharmaceutically acceptable salt thereof and after oral administration as directed a therapeutically effective amount of drug is released over a period of 6-24 hours; and
the composition maintains a slow release of drug even if the particles are crushed with a mortar and pestle and snorted.

10. The method of claim 9 wherein the molar ratio of fatty acid to drug is about 7:1 to about 5:1.

11. The method of claim 9, wherein the wax or wax-like substances are beeswax and carnauba wax and the fatty acid is myristic acid.

12. A method of making the tamper resistant pharmaceutical composition of claim 1, comprising:
    (a) dispersing or dissolving a drug prone to abuse in a mixture comprising one or more waxes, wax-like substances or mixtures thereof; and
    (b) forming a plurality of particles wherein the drug is present as a solid dispersion or solid solution within the particles and wherein the particles have a median particle size (D[0.5]) between about 200 microns and about 400 microns.

13. The method of claim 12, wherein said process comprises a spinning disc atomization process.

14. The composition of claim 1, wherein the particles have a median particle size (D[0.5]) between about 250 microns and about 400 microns.

15. The method of claim 9, wherein the particles have a median particle size (D[0.5]) between about 250 microns and about 400 microns.

16. The composition of claim 2, wherein the wax or wax-like substances are beeswax and carnauba wax, and the fatty acid is myristic acid.

17. The composition of claim 1 wherein oxycodone is present at about 9% by weight, the fatty acid is myristic acid, and the molar ratio of fatty acid to drug is about 8:1.

18. The composition of claim 1 wherein oxycodone is present at about 9% by weight, the fatty acid is myristic acid, the molar ratio of fatty acid to drug is about 8:1, and the wax or wax-like substances are present at about 36% by weight.

19. The composition of claim 18 wherein the wax or wax-like substances are yellow beeswax and carnauba wax.

* * * * *

UNITED STATES PATENT AND TRADEMARK OFFICE
CERTIFICATE OF CORRECTION

PATENT NO. : 10,004,729 B2
APPLICATION NO. : 15/606112
DATED : June 26, 2018
INVENTOR(S) : Roman V. Rariy et al.

Page 1 of 1

It is certified that error appears in the above-identified patent and that said Letters Patent is hereby corrected as shown below:

In the Claims

At Column 27, Claim number 2, Line number 67, please replace "fatty acid to drug is about 7:1 to about 5:1." with --fatty acid to drug is about 7:1 to about 15:1.--

At Column 28, Claim number 10, Line number 38, please replace "acid to drug is about 7:1 to about 5:1." with --acid to drug is about 7:1 to about 15:1.--

Signed and Sealed this
Twenty-third Day of July, 2019

Andrei Iancu
*Director of the United States Patent and Trademark Office*